(12) United States Patent
Herzog et al.

(10) Patent No.: US 8,877,966 B2
(45) Date of Patent: Nov. 4, 2014

(54) PROCESS FOR PREPARING ACRYLIC ACID FROM METHANOL AND ACETIC ACID

(75) Inventors: Stefanie Herzog, Mannheim (DE); Stefan Altwasser, Wachenheim (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/233,560

(22) Filed: Sep. 15, 2011

(65) Prior Publication Data

US 2012/0071688 A1 Mar. 22, 2012

Related U.S. Application Data

(60) Provisional application No. 61/383,363, filed on Sep. 16, 2010.

(30) Foreign Application Priority Data

Sep. 16, 2010 (DE) .......................... 10 2010 040 921

(51) Int. Cl.
| | | |
|---|---|---|
| *C07B 35/00* | (2006.01) | |
| *B01J 23/00* | (2006.01) | |
| *C07C 57/04* | (2006.01) | |
| *B01J 23/881* | (2006.01) | |
| *B01J 35/00* | (2006.01) | |
| *C07C 51/44* | (2006.01) | |
| *C07C 51/353* | (2006.01) | |
| *B01J 27/198* | (2006.01) | |
| *C07C 45/38* | (2006.01) | |
| *B01J 35/02* | (2006.01) | |
| *B01J 37/00* | (2006.01) | |

(52) U.S. Cl.
CPC ............... *C07C 45/38* (2013.01); *B01J 23/002* (2013.01); *B01J 2523/00* (2013.01); *B01J 35/023* (2013.01); *B01J 37/0045* (2013.01); *B01J 37/0009* (2013.01); *C07C 57/04* (2013.01); *B01J 23/881* (2013.01); *B01J 35/0006* (2013.01); *C07C 51/44* (2013.01); *C07C 51/353* (2013.01); *B01J 27/198* (2013.01); *C07B 2200/05* (2013.01)
USPC ......................................................... 562/599

(58) Field of Classification Search
None
See application file for complete search history.

(56) References Cited

U.S. PATENT DOCUMENTS

| | | | |
|---|---|---|---|
| 502,698 A | 8/1893 | Bouker | |
| 3,152,997 A | 10/1964 | Natta et al. | |
| 3,198,753 A | 8/1965 | Traina | |
| 3,408,309 A | 10/1968 | Gessner | |
| 3,716,497 A | 2/1973 | County | |
| 3,769,329 A | 10/1973 | Paulik et al. | |
| 3,846,341 A | 11/1974 | County | |
| 3,975,302 A | 8/1976 | Courty et al. | |
| 3,978,136 A * | 8/1976 | Friedrich et al. | 568/474 |
| 3,983,073 A * | 9/1976 | Trifiro et al. | 502/316 |
| 3,987,107 A | 10/1976 | McClellan et al. | |
| 3,994,977 A | 11/1976 | Aicher et al. | |
| 4,080,383 A | 3/1978 | Diem et al. | |
| 4,343,954 A | 8/1982 | Hoene | |
| 4,581,471 A * | 4/1986 | Barlow et al. | 560/210 |
| 4,584,412 A | 4/1986 | Aicher et al. | |
| 4,612,387 A | 9/1986 | Feitler | |
| 4,677,225 A | 6/1987 | Niizuma et al. | |
| 4,795,818 A | 1/1989 | Becker et al. | |
| 4,829,042 A | 5/1989 | Cavalli et al. | |
| 4,933,312 A | 6/1990 | Haddad et al. | |
| 5,001,259 A | 3/1991 | Smith et al. | |
| 5,095,125 A | 3/1992 | Haddad et al. | |
| 5,137,860 A | 8/1992 | Ebner et al. | |
| 5,158,923 A | 10/1992 | Barone | |
| 5,275,996 A | 1/1994 | Andrews et al. | |
| 5,296,436 A | 3/1994 | Bortinger | |
| 5,466,874 A | 11/1995 | Scates et al. | |
| 5,641,722 A | 6/1997 | Mitchell et al. | |
| 6,420,304 B1 | 7/2002 | Tsai et al. | |

FOREIGN PATENT DOCUMENTS

| | | |
|---|---|---|
| BE | 683130 | 12/1966 |
| CN | 101462069 A | 6/2009 |
| DE | 1 231 229 | 12/1966 |
| DE | 1 294 360 | 5/1969 |
| DE | 1 941 449 | 3/1970 |
| DE | 1 903 197 | 8/1970 |

(Continued)

OTHER PUBLICATIONS

U.S. Appl. No. 13/232,380, filed Sep. 14, 2011, Herzog, et al.
International Search Report issued Mar. 5, 2012 in patent application No. PCT/EP2011/065593 filed Sep. 9, 2011 with English translation of Category of Cited Documents.

*Primary Examiner* — Karl J Puttlitz

(74) *Attorney, Agent, or Firm* — Oblon, Spivak, McClelland, Maier & Neustadt, L.L.P.

(57) ABSTRACT

A process for preparing acrylic acid from methanol and acetic acid, in which, in a reaction zone A, the methanol is partially oxidized to formaldehyde in a heterogeneously catalyzed gas phase reaction, the product gas mixture A obtained and an acetic acid source are used to obtain a reaction gas input mixture B which comprises acetic acid and formaldehyde and has the acetic acid in excess over the formaldehyde, and the formaldehyde present in reaction gas input mixture B is aldol-condensed to acrylic acid under heterogeneous catalysis in a reaction zone B with acetic acid present in reaction gas input mixture B, and unconverted acetic acid still present alongside the acrylic acid target product in the product gas mixture B obtained is removed therefrom, and the acetic acid removed is recycled into the production of reaction gas input mixture B.

30 Claims, No Drawings

(56) References Cited

FOREIGN PATENT DOCUMENTS

| | | |
|---|---|---|
| DE | 1 618 413 | 10/1970 |
| DE | 2 145 851 | 3/1973 |
| DE | 23 34 981 | 1/1975 |
| DE | 24 42 311 | 3/1975 |
| DE | 25 33 209 | 2/1976 |
| DE | 35 20 053 A1 | 12/1985 |
| DE | 36 06 169 A1 | 8/1987 |
| DE | 38 89 233 T2 | 8/1994 |
| DE | 689 16 718 T2 | 1/1995 |
| DE | 198 54 575 A1 | 5/2000 |
| DE | 199 24 532 A1 | 11/2000 |
| DE | 199 27 624 A1 | 12/2000 |
| DE | 697 02 728 T2 | 2/2001 |
| DE | 102 35 847 A1 | 8/2003 |
| DE | 103 36 386 A1 | 3/2004 |
| DE | 102 43 625 A1 | 4/2004 |
| DE | 103 61 456 A1 | 7/2005 |
| DE | 10 2004 004 496 A1 | 8/2005 |
| DE | 10 2004 017 150 A1 | 10/2005 |
| DE | 10 2004 057 868 A1 | 6/2006 |
| DE | 10 2004 057 874 A1 | 6/2006 |
| DE | 10 2005 035 978 A1 | 2/2007 |
| DE | 10 2005 062 929 A1 | 7/2007 |
| DE | 10 2006 024 901 A1 | 11/2007 |
| DE | 10 2007 005 606 A1 | 4/2008 |
| DE | 10 2007 004 960 A1 | 7/2008 |
| DE | 10 2008 040 093 A1 | 12/2008 |
| DE | 10 2008 040 094 A1 | 1/2009 |
| DE | 10 2007 055 086 A1 | 5/2009 |
| DE | 10 2009 027 401 A1 | 2/2010 |
| DE | 10 2008 060 310 A1 | 6/2010 |
| DE | 10 2010 028 328 A1 | 11/2011 |
| DE | 10 2010 023 312 A1 | 12/2011 |
| EP | 0 055 618 A1 | 7/1982 |
| EP | 0 087 870 A1 | 9/1983 |
| EP | 0 122 782 A1 | 10/1984 |
| EP | 0 161 874 A1 | 11/1985 |
| EP | 0 164 614 | 12/1985 |
| EP | 0 199 359 A2 | 10/1986 |
| EP | 0 277 824 A2 | 8/1988 |
| EP | 0 551 111 A1 | 7/1993 |
| EP | 0 596 632 A1 | 5/1994 |
| EP | 0 656 811 B1 | 3/1996 |
| EP | 0 700 714 A1 | 3/1996 |
| EP | 0656811 * | 3/1996 |
| EP | 0 714 700 A2 | 6/1996 |
| EP | 0 778 255 A1 | 6/1997 |
| EP | 1 651 344 A0 | 5/2006 |
| EP | 1 506 151 B1 | 6/2010 |
| EP | 2 213 370 A2 | 8/2010 |
| EP | 2 220 004 | 8/2010 |
| WO | WO 95/26817 | 10/1995 |
| WO | WO 97/12674 | 4/1997 |
| WO | WO 01/68245 A1 | 9/2001 |
| WO | WO 01/77056 A1 | 10/2001 |
| WO | WO 03/053556 A2 | 7/2003 |
| WO | WO 03/078310 A2 | 9/2003 |
| WO | WO 2004/007405 A1 | 1/2004 |
| WO | WO 2005/042459 A1 | 5/2005 |
| WO | 2005063375 * | 7/2005 |
| WO | WO 2005/063375 A1 | 7/2005 |
| WO | WO 2005/093010 A2 | 10/2005 |
| WO | WO 2006/094765 A1 | 9/2006 |
| WO | WO 2007/012620 A1 | 2/2007 |
| WO | WO 2007/059974 A1 | 5/2007 |
| WO | WO 2008/023040 A2 | 2/2008 |
| WO | WO 2008/087116 A1 | 7/2008 |
| WO | WO 2008/116840 A1 | 10/2008 |
| WO | WO 2008/152079 A1 | 12/2008 |
| WO | WO 2009/149809 A1 | 12/2009 |
| WO | WO 2010/000720 A2 | 1/2010 |
| WO | WO 2010/000764 A2 | 1/2010 |
| WO | WO 2010/022923 A1 | 3/2010 |
| WO | WO 2010/034480 A2 | 4/2010 |
| WO | WO 2010/060236 A1 | 6/2010 |
| WO | WO 2010/060279 A1 | 6/2010 |
| WO | WO 2010/062936 A1 | 6/2010 |
| WO | WO 2010/067945 A1 | 6/2010 |
| WO | WO 2010/072424 A1 | 7/2010 |
| WO | WO 2010/072721 A2 | 7/2010 |
| WO | WO 2010/072723 A2 | 7/2010 |
| WO | WO 2010/074177 A1 | 7/2010 |

* cited by examiner

PROCESS FOR PREPARING ACRYLIC ACID FROM METHANOL AND ACETIC ACID

The present invention relates to a process for preparing acrylic acid from methanol and acetic acid. The present invention also relates to the preparation of conversion products from acrylic acid thus obtained.

At present, acrylic acid is prepared on the industrial scale essentially exclusively by heterogeneously catalyzed two-stage partial oxidation of propylene (see, for example, DE-A 103 36 386).

One advantage of this procedure is that it has a comparatively high target product selectivity based on propylene converted, which, in the case of recycling of propylene unconverted in single pass, enables high acrylic acid yields from the propylene used. Furthermore, propylene has extremely economically viable backward integration to the base fossil raw material, mineral oil (i.e. propylene can be produced from mineral oil with comparatively low production costs), which enables inexpensive acrylic acid preparation overall.

In view of the foreseeable shortage in the fossil resource of mineral oil, there will, however, be a need in the future for processes for preparing acrylic acid from raw materials, which can be performed in a comparatively economically viable manner even without backward integration thereof to the base fossil raw material, mineral oil, and which at the same time have backward integration of the raw materials thereof to base raw materials whose lifetimes extend beyond that of mineral oil.

WO 2005/093010 considers propylene itself to be such a raw material. It proposes continuing, in the future, with the two-stage heterogeneously catalyzed partial gas phase oxidation of propylene to acrylic acid, but obtaining the propylene required from methanol. The advantage of such a procedure is that methanol is obtainable both proceeding from base fossil raw materials such as coal, for example brown coal and hard coal; cf., for example, WO 2010/072424) and natural gas (cf., for example, WO 2010/067945), both of which have a much longer lifetime than mineral oil, and proceeding from the renewable base raw material of biomass, and also directly from the carbon dioxide present in the earth's atmosphere (in each case optionally with additional use of steam or molecular hydrogen) (cf., for example, G. A. Olah et al., Beyond Oil and Gas; The Methanol Economy, Wiley-VCH, 2009).

However, a disadvantage of the procedure proposed in WO 2005/093010 is that the selectivity of obtaining propylene proceeding from methanol with the preparation processes currently known, based on methanol converted, is less than 70 mol %, which is unsatisfactory (in addition to propylene, for example, ethylene and butylene are also formed).

In this document, base fossil raw materials shall be understood to mean base raw materials which, like brown coal, hard coal, natural gas and mineral oil, for example, are formed from degradation products of dead plants and dead animals in geological prehistory.

In contrast, in this document, renewable raw materials shall be understood to mean those raw materials which are obtained from fresh biomass, i.e. from (new) vegetable and animal material which is being newly grown (in the present) and will be grown in the future.

There have also already been proposals (for example in WO 2008/023040) to prepare acrylic acid and the conversion products thereof proceeding from the renewable raw material glycerol. However, a disadvantage of such a procedure is that glycerol is obtainable economically as a renewable raw material essentially only as a coproduct of biodiesel production. This is disadvantageous in that the current energy balance of biodiesel production is unsatisfactory.

Furthermore, the prior art has proposed the preparation of acrylic acid from propane (for example in DE-A 102006024901), which constitutes a raw constituent of natural gas. However, a disadvantage of such a method of preparation of acrylic acid is firstly the comparatively high unreactiveness of propane, and the fact that propane also constitutes a sought-after energy carrier with good manageability.

It was therefore an object of the present invention to provide an alternative process for preparing acrylic acid, which does not have the described disadvantages of the prior art processes, and especially has a satisfactory selectivity of target product formation proceeding from the raw materials used for preparation thereof.

Accordingly, a process for preparing acrylic acid from methanol and acetic acid is provided.

The appeal of such a procedure is especially that the acetic acid is itself obtainable in a simple and industrially tried and tested manner proceeding from methanol, by carbonylation thereof with carbon monoxide (cf., for example, Industrielle Organische Chemie [Industrial Organic Chemistry], Klaus Weissermel and Hans-Jürgen Arpe, Wiley-VCH, Weinheim, 5th edition (1998), p. 194 to 198).

Overall, a process for preparing acrylic acid from methanol is thus essentially provided. In contrast to the process of WO 2005/093010, likewise based on the raw material methanol, the process according to the invention possesses an increased selectivity of acrylic acid formation based on the amount of methanol converted.

The advantage of an acrylic acid preparation process based essentially exclusively on the raw material methanol is not least because the methanol can be obtained via synthesis gas (gas mixtures of carbon monoxide and molecular hydrogen) in principle from all carbonaceous base fossil materials and all carbonaceous renewable raw materials (as in the case of methane, the molecular hydrogen required (a process for obtaining methane from biogas or biomass is described, for example, by DE-A 102008060310 or EP-A 2220004) may already be present in the carbon carrier; an alternative hydrogen source available is water, from which molecular hydrogen can be obtained, for example, by means of electrolysis; the oxygen source is generally air; cf., for example, WO 10-060236 and WO 10-060279). A suitable renewable carbonaceous raw material is, for example, lignocellulose for synthesis gas production (cf., for example, WO 10-062936). It is also possible to obtain synthesis gas by coupling the pyrolysis of biomass directly with steam reforming.

The present invention thus provides a process for preparing acrylic acid from methanol and acetic acid, which comprises the following measures:

a stream of a reaction gas input mixture A comprising the methanol and molecular oxygen reactants and at least one inert diluent gas other than steam is conducted through a first reaction zone A charged with at least one oxidation catalyst A and, in the course of passage through reaction zone A, methanol present in the reaction gas input mixture A is oxidized under heterogeneous catalysis to formaldehyde and steam so as to form a product gas mixture A comprising formaldehyde, steam and at least one inert diluent gas other than steam, with or without excess molecular oxygen, and a stream of product gas mixture A leaves reaction zone A, it optionally being possible to supply further molecular oxygen and/or further inert diluent gas to the reaction gas mixture A flowing through reaction zone A on its way through reaction zone A, optionally, the stream of product gas mixture A leaving reaction zone A is fed to a separation zone T* and any unconverted methanol still present in product gas mixture A in separation zone T* is removed from product gas mixture A to leave a formaldehyde-comprising product gas mixture A*, and a stream of product gas mixture A* leaves reaction zone A, a stream of a reaction gas input mixture B which comprises acetic acid, steam, at least one inert diluent gas other than steam and formaldehyde, with or without molecular oxygen, and in which the molar amount $n_{HAc}$ of acetic acid present is greater than the molar amount $n_{Fd}$ of formaldehyde present therein is obtained from the stream of product gas mixture A or from the stream of product gas mixture A* and at least one further stream comprising acetic acid, the stream of reaction gas input mixture B is passed through a second reaction zone B charged with at least one aldol condensation catalyst B and formaldehyde present in reaction gas input mixture B, as it flows through reaction zone B, is condensed with acetic acid present in reaction gas input mixture B under heterogeneous catalysis to give acrylic acid and $H_2O$, so as to form a product gas mixture B comprising acrylic acid, acetic acid, steam and at least one inert diluent gas other than steam, with or without molecular oxygen, and a stream of product gas mixture B leaves reaction zone B, it optionally being possible to supply further molecular oxygen and/or further inert diluent gas to the reaction gas mixture B flowing through reaction zone B on its way through reaction zone B, the stream of product gas mixture B leaving reaction zone B is fed to a separation zone T and separated in separation zone T into at least three streams X, Y and Z, the acrylic acid flow present in stream X being greater than the acrylic acid flow present in streams Y and Z together, the acetic acid flow present in stream Y being greater than the acetic acid flow present in streams X and Z together, the flow of inert diluent gas other than steam present in stream Z being greater than the flow of inert diluent gas other than steam present in streams X and Y together, and stream Y is recycled into reaction zone B and used to obtain reaction gas input mixture B.

A significant advantage of the inventive procedure arises from the fact that the formaldehyde present in product gas mixture A need not be removed from product gas mixture A in order to be able to use it to obtain reaction gas input mixture B.

Instead, the formaldehyde-comprising stream of product gas mixture A leaving reaction zone A can be used as such (i.e. without conducting a removal process thereon beforehand) in order to obtain reaction gas input mixture B. In general, for this purpose, product gas mixture A will first be cooled (quenched) when it leaves reaction zone A in order to reduce unwanted further reactions in product gas mixture A before the introduction thereof into reaction gas input mixture B. Typically, it will be cooled as rapidly as possible to temperatures of 150 to 350° C., or 200 to 250° C.

Optionally, however, it is also possible first to remove a portion or the entirety of any methanol which has not been converted in reaction zone A and is still present in product gas mixture A from the latter in a separation zone T*, and then to use the remaining formaldehyde-comprising product gas mixture A* (which may pass through the liquid state in the course of the removal) to obtain reaction gas input mixture B. Advantageously in application terms, the removal will be undertaken by rectificative means. For this purpose, product gas mixture A, optionally after preceding direct or indirect cooling, can be fed in gaseous form to the corresponding rectification column provided with cooling circuits. It is of course possible, however, first to convert those constituents whose boiling point at standard pressure ($10^5$ Pa) is less than or equal to the boiling point of formaldehyde from product gas mixture A to the liquid phase (for example by condensation), and to undertake the rectification from the liquid phase. In general, such a methanol removal is also accompanied by a removal of steam present in product gas mixture A. For the purpose of the aforementioned direct cooling, it is possible to use, for example, liquid phase which has been withdrawn from the bottom region of the rectification column and has optionally additionally been cooled by indirect heat exchange, which is sprayed by means of appropriate nozzles into fine droplets which provide the large heat exchange area required for the hot product gas mixture A. Appropriately in accordance with the invention, the methanol removed will be recycled into reaction zone A and used to obtain reaction gas input mixture A (cf. DE-A 1618413). A removal of methanol from product gas mixture A prior to the use thereof to obtain reaction gas input mixture B is generally undertaken when reaction zone A is configured such that the resulting conversion of methanol in reaction zone A, based on the single pass of product gas mixture A through reaction zone A, is not more than 90 mol %. It will be appreciated that such a methanol removal, however, can also be employed in the case of corresponding methanol conversions of not more than 95 mol %. For example, such a methanol removal can be undertaken as described in Ullmann's Encyclopedia of Industrial Chemistry, vol. A11, 5th ed., VCH Weinheim on page 626 ff.

The oxidation catalysts A particularly suitable for charging of reaction zone A can be divided essentially into two groups.

The first of the two groups comprises what are called the silver catalysts, which have, as the active material, elemental silver whose purity is preferably ≥99.7% by weight, advantageously ≥99.8% by weight, preferably ≥99.9% by weight and most preferably ≥99.99% by weight. The corresponding processes for heterogeneously catalyzed partial gas phase oxidation of methanol to formaldehyde over these "silver catalysts" are described in the prior art as silver processes (cf., for example, "A. Nagy, G. Mestl: High temperature partial oxidation reactions over silver catalysts, Appl. Catal. 188 (1999), p. 337 to 353", "H. Schubert, U. Tegtmayr, R. Schlögl: On the mechanism of the selective oxidation of methanol over elemental silver, Catalyst Letters, 28 (1994), p. 383 to 395", "L. Lefferts, Factors controlling the selectivity of silver catalysts for methanol oxidation, thesis, University of Twente (1987)" and DE-A 2334981).

Silver oxidation catalysts A advantageous in accordance with the invention for charging of reaction zone A are disclosed, for example, in Ullmann's Encyclopedia of Industrial Chemistry, vol. A11, 5th ed., VCH, Weinheim, p. 619 to 652, or in Encyclopedia of Chemical Technology, vol. 11, 4th ed., Wiley & Sons, New York, p. 929 to 949, in DE-B 1231229, in DE-B 1294360, in DE-A 1903197 and in BE patent 683130. Typically, these comprise crystals (the shape of which may also be round) of elemental silver (preferably of the abovementioned purity) which have been deposited by electrolysis of aqueous silver salt solutions and which can be poured as a fixed catalyst bed onto a perforated base (for example a perforated plate, a sieve or a mesh network (preferably likewise manufactured from silver)) (typical bed heights are 10 to 50 mm, frequently 15 to 30 mm). The total content of metals present in elemental form other than silver in the catalytically active silver (e.g. Cu, Pd, Pb, Bi, Fe, Pt and Au) is advantageously ≥2000 ppm by weight, better ≥1000 ppm by weight, preferably ≥100 ppm by weight and more preferably ≥50 ppm by weight or ≥30 ppm by weight. The longest dimension of the silver crystals is typically in the range from 0.1 to 5 mm and preferably increases in flow direction of reaction gas mixture A. The fixed silver bed is preferably configured as a two-layer bed, in which case the lower layer has a thickness, for example, of 15 to 40 mm, preferably 20 to 30 mm, and consists to an extent of at least 50% by weight of silver crystals of particle size 1 to 4 mm, preferably 1 to 2.5 mm. The upper layer may have, for example, a thickness (layer thickness) of 0.75 to 3 mm, preferably 1 to 2 mm, and consist of crystals having particle sizes (longest dimensions) of 0.1 to 1 mm, preferably 0.2 to 0.75 mm. In this case, reaction gas input mixture A flows in from the top downward.

In order to counteract sintering of the silver crystals with increasing operating time (at comparatively high reaction temperatures), which reduces the performance of the fixed catalyst bed, WO 2010/022923 recommends coating the silver crystals with a thin porous layer of oxidic material of at least one of the elements Al, Si, Zr and Ti (the layer thickness may be 0.3 to 10 µm, preferably 1.0 to 5.0 µm, more preferably 2.0 to 4.0 µm and at best about 3 µm), and in this way achieving prolonging of the service life of the fixed catalyst bed.

The methanol content in reaction gas input mixture A is, in the silver process, normally at least 5% by volume, usually at least 10% by volume, and may extend up to 60% by volume. The aforementioned methanol content in the silver process is preferably 15 to 50% by volume and more preferably 20 to 40 or to 30% by volume.

In addition, the ratio of the molar amount of molecular oxygen present in reaction gas input mixture A ($n_o$) to the molar amount of methanol present in reaction gas input mixture A ($n_{Me}$), $n_o:n_{Me}$, in the silver process is normally less than 1 (<1), preferably ≤0.8. It will more preferably be 0.2 to 0.6 and most preferably 0.3 to 0.5 or 0.4 to 0.5. In general, $n_o:n_{Me}$ in the silver process will not be less than 0.1.

In this document, an inert diluent gas shall be understood to mean a reaction gas input mixture constituent which behaves inertly under the conditions in the particular reaction zone A, B and—viewing each inert reaction gas constituent alone—remains chemically unchanged in the particular reaction zone to an extent of more than 95 mol %, preferably to an extent of more than 97 mol %, or to an extent of more than 98 mol %, or to an extent of more than 99 mol %.

Examples of inert diluent gases both for reaction zone A and reaction zone B are $H_2O$, $CO_2$, $N_2$ and noble gases such as Ar, and mixtures of the aforementioned gases. One task assumed by the inert diluent gases is that of absorbing heat of reaction released in the reaction zone A, thus limiting what is called the hotspot temperature in reaction zone A and having a favorable effect on the ignition behavior of reaction gas mixture A. The hotspot temperature is understood to mean the highest temperature of reaction gas mixture A on its way through reaction zone A.

A preferred inert diluent gas other than steam in the case of the silver process for reaction gas input mixture A is molecular nitrogen. The advantage thereof is based not least on the fact that molecular nitrogen occurs in air as a natural companion of molecular oxygen, which makes air a preferred source of the molecular oxygen required in reaction zone A. It will be appreciated that, in the case of the silver process, it is, however, also possible in accordance with the invention to use pure molecular oxygen, or air enriched with molecular oxygen, or another mixture of molecular oxygen and inert diluent gas, as the oxygen source.

Typically, reaction gas input mixture A comprises, in the case of the silver process, 20 to 80% by volume, or 30 to 70% by volume, or 40 to 60% by volume, of inert diluent gas. The latter may be entirely free of steam. In other words, reaction gas input mixture A in the case of the silver process may comprise 20 to 80% by volume, or 30 to 70% by volume, or 40 to 60% by volume, of molecular nitrogen.

In principle, reaction gas input mixture A in the case of the silver process may comprise >0 to 50% by volume of $H_2O$.

Steam is advantageous as a constituent of reaction gas input mixture A in that steam, compared to $N_2$ and noble gases for example, has an increased molar heat capacity. In general, steam as a constituent of reaction gas mixture A is also beneficial for the desorption of the desired partial oxidation product from the catalyst surface, which has a positive effect on the selectivity of the desired product formation. Since presence of steam in reaction zone B, however, generally reduces the desired aldol condensation to a certain extent and also increases the energy expenditure required to remove a stream X comprising enriched acrylic acid from product gas mixture B in separation zone T (acrylic acid has an elevated affinity for $H_2O$), appropriately in accordance with the invention, comparatively limited steam contents of reaction gas input mixture A are preferred.

In other words, reaction gas input mixture A in the silver process preferably comprises ≥5 to 45% by volume of $H_2O$, advantageously ≥10 to 40% by volume and particularly advantageously 15 to 35% by volume, or 20 to 30% by volume of $H_2O$. The boiling point of the inert diluent gases other than steam (based on a pressure of $10^5$ Pa=1 bar) is normally well below that of steam (based on the same pressure), and therefore stream Z in the process according to the invention generally comprises the inert diluent gases other than steam (e.g. $N_2$ and $CO_2$) in enriched form.

Advantageously in application terms, the separation of product gas mixture B in separation zone T will be performed in such a way that stream Z also has an appropriate content of steam. In the latter case, stream Z may function both as a source for inert gases other than steam and for steam.

The inert gas source used in the silver process for reaction gas input mixture A may thus also be the stream Z obtained in separation zone T. Appropriately in application terms, therefore, in the silver process, a substream of stream Z will be recycled into reaction zone A to obtain reaction gas input mixture A (cycle gas method). It will be appreciated that a portion of stream Z may also be recycled into reaction zone B.

In other words, reaction gas input mixtures A suitable in accordance with the invention may, in the silver process, comprise, for example, 10 to 50% by volume of $H_2O$ and 20 to 60% by volume of inert diluent gas other than steam (e.g. $N_2$, or $N_2+CO_2$, or $N_2$+noble gas (e.g. Ar), or $N_2+CO_2$+noble gas (e.g. Ar)).

It will be appreciated that reaction gas input mixtures A in the silver process may also comprise 10 to 40% by volume of $H_2O$ and 30 to 60% by volume of inert diluent gases other than steam (for example those mentioned above).

Of course, reaction gas input mixture A, in the silver process, may also comprise 20 to 40% by volume of $H_2O$ and 30 to 50% by volume of inert diluent gases other than steam (for example those mentioned above).

In principle, in the case of the silver process, reaction gas mixture A can be either forced or sucked through reaction zone A. Accordingly, the working pressure in the case of the silver process within reaction zone A may be either ≥$10^5$ Pa or <10⁵ Pa. Appropriately in application terms, the working pressure in the case of the silver process in reaction zone A will be $10^3$ to $10^6$ Pa, preferably $10^4$ to $5 \cdot 10^5$ Pa, more preferably $10^4$ to $2 \cdot 10^5$ Pa and most preferably $0.5 \cdot 10^5$ Pa to $1.8 \cdot 10^5$ Pa.

The temperature of reaction gas mixture A (the term "reaction gas mixture A" comprises, in the present application, all gas mixtures which occur in reaction zone A and are between reaction gas input mixture A and product gas mixture A) will, in the case of the silver process, within reaction zone A, normally be within the range from 400 to 800° C., preferably within the range from 450 to 800° C. and more preferably within the range from 500 to 800° C. The term "temperature of reaction gas mixture A" (also referred to in this document as reaction temperature in reaction zone A) means primarily that temperature which reaction gas mixture A has from attainment of a conversion of the methanol present in reaction gas input mixture A of at least 5 mol % until attainment of the corresponding final conversion of the methanol within reaction zone A.

Advantageously in accordance with the invention, the temperature of reaction gas input mixture A in the case of the silver process is within the aforementioned temperature ranges over the entire reaction zone A.

Advantageously, in the case of the silver process, reaction gas input mixture A is also supplied to reaction zone A already with a temperature within the aforementioned range. Frequently, in the case of the silver process, a charge of reaction zone A with solid inert material or of catalytically active catalyst charge highly diluted with such inert material is present at the inlet into reaction zone A upstream in flow direction of the actually catalytically active catalyst charge (which may also be diluted with inert shaped bodies). As it flows through such an upstream charge of reaction zone A, the temperature of the reaction gas input mixture A supplied to reaction zone A in the case of the silver process can be adjusted comparatively easily to the value with which reaction gas mixture A in the case of the silver process is to enter the actual catalytically active catalyst charge of reaction zone A.

When the temperature of reaction gas mixture A in the case of the silver process within reaction zone A is limited to values of 450 to 650-° C., preferably 500 to 600-° C., the conversion of methanol will generally be ≤90 mol %, frequently ≤85 mol % or ≤80 mol %, while the selectivity of formaldehyde formation will be at values of ≥90 mol %, in many cases ≥93 mol % or ≥95 mol %. In this case (in which the steam content of the reaction gas input mixture is preferably <10% by volume), it is appropriate in accordance with the invention, from product gas mixture A, to remove at least a portion of unconverted methanol prior to the use thereof for obtaining reaction gas input mixture B, and to recycle it into the production of reaction gas input mixture A.

Advantageously in accordance with the invention, the temperature of reaction gas mixture A in the case of the silver process within reaction zone A will therefore be 550 to 800-° C., preferably 600 to 750-° C. and more preferably 650 to 750-° C.

At the same time, the steam content of reaction gas input mixture A in the case of the silver process is advantageously adjusted to values of ≥10% by volume, preferably ≥15% by volume and particularly advantageously ≥20% by volume. Both the elevated temperature and the elevated steam content of reaction gas input mixture A, in the case of the silver process, have an advantageous effect on the methanol conversion (based on a single pass of reaction gas mixture A through reaction zone A). In general, this conversion will be >90 mol %, in many cases ≥92 mol %, or ≥95 mol % and frequently even ≥97 mol % (cf., for example, Ullmann's Encyclopedia of Industrial Chemistry, vol. A 11, 5th ed., VCH Weinheim on pages 625 ff.) (the high methanol conversions which are to be achieved in the case of the silver process in spite of the comparatively low $n_o{:}n_{Me}$ ratios in reaction gas input mixture A are attributable in particular to the fact that, with increasing temperature of reaction gas mixture A in reaction zone A, the exothermic partial oxidation $CH_3OH + 0.5\ O_2 \rightarrow HCHO + H_2O$ is increasingly accompanied by the endothermic dehydration $CH_3OH \leftrightarrows HCHO + H_2$). In this way, in the case of the silver process, it is regularly possible to achieve yields of formaldehyde of ≥85 mol %, usually ≥87 mol % and in many cases ≥89 mol % based on a single pass of reaction gas mixture A through reaction zone A and the molar amount of methanol converted. Otherwise, the silver process can be performed as described in the prior art documents already mentioned in this regard, or as described in documents U.S. Pat. No. 4,080,383, U.S. Pat. No. 3,994,977, U.S. Pat. No. 3,987,107, U.S. Pat. No. 4,584,412 and U.S. Pat. No. 4,343,954. It will be appreciated that, in the case of the silver process described, it is possible not only to use comparatively pure methanol as the raw material (source). Methanol raw materials suitable in accordance with the invention in this regard are also aqueous methanol solutions and technical-grade methanol, which can be used after appropriate evaporation to obtain reaction gas input mixture A.

Suitable reactors for execution of the silver process in reaction zone A include not only those recommended in the aforementioned prior art but also heat exchanger reactors.

A heat exchanger reactor has at least one primary space and at least one secondary space, which are separated from one another by a dividing wall. The catalyst charge positioned in the at least one primary space comprises at least one oxidation catalyst A, and reaction gas mixture A flows through it. At the same time, a fluid heat carrier flows through the secondary space and heat exchange takes place between the two spaces through the dividing wall, which pursues the purpose of monitoring and controlling the temperature of reaction gas mixture A on its way through the catalyst bed (of controlling the temperature of reaction zone A).

Examples of heat exchanger reactors suitable in accordance with the invention for the implementation of reaction zone A are the tube bundle reactor (as disclosed, for example, in EP-A 700714 and the prior art cited in that document) and the thermoplate reactor (as disclosed, for example, in documents EP-A 1651344, DE-A 10361456, DE-A 102004017150 and the prior art acknowledged in these documents). In the case of the tube bundle reactor, the catalyst bed through which reaction gas mixture A flows is preferably within the tubes thereof (the primary spaces), and at least one heat carrier is conducted through the space surrounding the reaction tubes (the secondary space). Useful heat carriers for the heat exchanger reactors are, for example, salt melts, heat carrier oils, ionic liquids and steam. In general, tube bundle reactors used on the industrial scale comprise at least three thousand up to several tens of thousands of reaction tubes connected in parallel (reactor tubes). It will be appreciated that the configuration of reaction zone A can also be implemented in a fluidized bed reactor or a micro reactor.

Conventional reactors and micro reactors differ by their characteristic dimensions and especially by the characteristic dimensions of the reaction space which accommodates the catalyst bed through which the reaction gas mixture flows.

The space velocity of methanol present in reaction gas input mixture A on the reactor charged with silver crystals will generally be (0.5 to 6)·10³ kg of methanol per m² of reactor cross section or cross section of the fixed catalyst bed.

Preferably in accordance with the invention, the heterogeneously catalyzed partial gas phase oxidation of methanol to formaldehyde in reaction zone A will, however, be performed by the FORMOX process.

In contrast to the silver process, the FORMOX process is performed over oxidation catalysts A whose active material is a mixed oxide which has at least one transition metal in the oxidized state (cf., for example, WO 03/053556 and EP-A 2213370). The term "transition metals" means the chemical elements of the Periodic Table with atomic numbers 21 to 30, 39 to 48 and 57 to 80.

Preferably in accordance with the invention, aforementioned mixed oxide active materials comprise at least one of the transition metals Mo and V in the oxidized state. Most preferably in accordance with the invention, the aforementioned active materials are mixed oxides having at least the elements Fe and Mo in the oxidized state (cf., for example, U.S. Pat. Nos. 3,983,073, 3,978,136, 3,975,302, 3,846,341, 3,716,497, 4,829,042, EP-A 2213370 and WO 2005/063375, U.S. Pat. Nos. 3,408,309, 3,198,753, 3,152,997, WO 2009/1489809, DE-A 2145851, WO 2010/034480, WO 2007/059974 and "Methanol Selective Oxidation to Formaldehyde over Iron-Molybdate Catalysts, Ana Paula Vieira Soares and Manuel Farinha Portela and Alain Kiennemann in Catalysis Review 47, pages 125 to 174 (2004)" and the prior art cited in these documents).

A further difference between the silver process and the FORMOX process is that the ratio of the molar amount of molecular oxygen present in reaction gas input mixture A ($n_o$) to the molar amount of methanol present in reaction gas input mixture A ($n_{Me}$), $n_o$:$n_{Me}$, is normally at least 1 or greater than 1 (≥1), preferably ≥1.1. In general, the $n_o$ : $n_{Me}$ ratio in reaction gas input mixture A in the FORMOX process will, however, be not more than 5, frequently not more than 4. $n_o$:$n_{Me}$ ratios which are advantageous in accordance with the invention in reaction gas input mixture A are 1.5 to 3.5, preferably 2 to 3. An oxygen excess is advantageous in accordance with the invention in that, in the inventive procedure, it is introduced via product gas mixture A into reaction gas input mixture B, and hence into reaction zone B, which has an advantageous effect on the service life of the aldol condensation catalyst B. In addition, the methanol content of reaction gas input mixture A in the FORMOX process will typically be not more than 15% by volume, usually not more than 11% by volume. This is because gas mixtures of molecular nitrogen, molecular oxygen and methanol with a molecular oxygen content of not more than approx. 11% by volume of molecular oxygen are outside the explosion range. Normally, the methanol content in reaction gas input mixture A in the case of the FORMOX process will be 2% by volume, preferably 4 to 10% by volume and more preferably 6 to 9% by volume or 5 to 7% by volume. Gas mixtures of molecular nitrogen, molecular oxygen and methanol whose methanol content is ≤6.7% by volume are, irrespective of the molecular oxygen content therein, outside the explosion range, which is why particularly high $n_o$:$n_{Me}$ ratios in reaction gas input mixture A can be employed within this concentration range.

However, the FORMOX process also differs from the silver process in that the methanol conversions achieved by this process, based on a single pass of reaction gas mixture A through reaction zone A, essentially irrespective of the inert diluent gas used in reaction gas input mixture A, are regularly >90 mol %, typically ≥92 mol %, usually ≥95 mol % and in many cases even ≥97 mol % or ≥98 mol %, or ≥99 mol %. The accompanying selectivities of formaldehyde formation are regularly ≥90 mol %, usually ≥92 mol % and in many cases ≥94 mol %, and frequently even ≥96 mol %.

According to the invention, useful inert diluent gases in reaction gas input mixture A for the FORMOX process (and for the silver process) in reaction zone A are likewise gases such as $H_2O$, $N_2$, $CO_2$ and noble gases such as Ar, and mixtures of aforementioned gases. A preferred inert diluent gas other than steam in the case of the FORMOX process too in reaction gas input mixture A is molecular nitrogen.

The inert diluent gas content in reaction gas input mixture A may, in the case of the FORMOX process, be 70 to 95% by volume, frequently 70 to 90% by volume and advantageously 70 to 85% by volume. In other words, the molecular nitrogen content of reaction gas input mixture A may, in the case of employment of the FORMOX process, in reaction gas input mixture A, be 70 to 95% by volume, or 70 to 90% by volume, or 70 to 85% by volume. Advantageously in accordance with the invention, reaction gas input mixture A in the case of the FORMOX process may be free of steam. Appropriately in application terms, reaction gas input mixture A, in the case of employment of a FORMOX process in reaction zone A, may have a low steam content for the same reasons as in the case of the silver process. In general, the steam content of reaction gas input mixture A in the FORMOX process in reaction zone A is ≥0.1% by volume and ≤20% by volume or ≤10% by volume, advantageously ≥0.2% by volume and ≤7% by volume, preferably ≥0.5% by volume and ≤5% by volume.

A further advantage of the employment of a FORMOX process in reaction zone A, in accordance with the invention, results from the fact that the high methanol conversions described are established at significantly lower reaction temperatures compared to the use of a silver process.

The temperature of reaction gas mixture A in the case of the FORMOX process in reaction zone A will normally be in the range from 250 to 500-° C., preferably in the range from 300 to 450-° C. and frequently within the range from 270 to 400-° C. The meaning of the term "temperature of reaction gas mixture A" corresponds in the case of the FORMOX process to that which has already been given in this document for the silver process.

Advantageously in accordance with the invention, the temperature of reaction gas mixture A (also referred to in this document as the reaction temperature in reaction zone A) in the case of the FORMOX process, over the entire reaction zone A, is within the aforementioned temperature ranges. Advantageously, in the case of the FORMOX process too, reaction gas input mixture A is supplied to reaction zone A already with a temperature within the aforementioned range. Frequently, in the case of the FORMOX process, a charge of reaction zone A with solid inert material or of catalytically active catalyst charge highly diluted with such inert material is present at the inlet into reaction zone A upstream in flow direction of the actual catalytically active catalyst charge (which may also be diluted with inert shaped bodies). As it flows through such an upstream charge of reaction zone A, the temperature of reaction gas input mixture A supplied to reaction zone A in the FORMOX process can be adjusted in a comparatively simple manner to the value with which reaction gas mixture A in the FORMOX process is to enter the actual catalytically active catalyst charge of reaction zone A.

With regard to the working pressure in reaction zone A, the statements made for the silver process apply correspondingly to the FORMOX process.

Mixed oxide active materials particularly suitable for the FORMOX process are those of the general formula I

in which the variables are each defined as follows:
$M^1$=Mo and/or Fe, or
Mo and/or Fe and, based on the total molar amount of Mo and Fe, a total molar amount of up to 10 mol % (e.g. 0.01 to 10 mol %, or 0.1 to 10 mol %), preferably not more than 5 mol %, of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B, q=0 to 5, or 0.5 to 3, or 1 to 2, m=1 to 3, and n=1 to 6, with the proviso that the contents of both sets of square brackets are electrically uncharged, i.e. do not have any electrical charge.

Advantageously in accordance with the invention, mixed oxide active materials I comprise less than 50 mol %, more preferably less than 20 mol % and more preferably less than 10 mol % of the Fe present in the mixed oxide active material I in the +2 oxidation state, and the remaining amount of the Fe present therein in each case in the +3 oxidation state. Most preferably, the mixed oxide active material I comprises all of the Fe present therein in the +3 oxidation state.

The $n_{Mo}:n_{Fe}$ ratio of molar amount of Mo present in a mixed oxide active material I ($n_{Mo}$) to molar amount of Fe present in the same mixed oxide active material ($n_{Fe}$) is preferably 1:1 to 5:1.

In addition, it is advantageous in accordance with the invention when $M^1$=Mo and m=1 and n=3. Mixed oxide active materials advantageous in accordance with the invention also exist when $M^1$=Fe and m=2 and n=3.

Mixed oxide active materials I favorable in accordance with the invention are also those with such a stoichiometry that they can be considered (represented) in a formal sense as a mixture of $MoO_3$ and $Fe_2O_3$, and the $MoO_3$ content of the mixture is 65 to 95% by weight and the $Fe_2O_3$ content of the mixture is 5 to 35% by weight.

Mixed oxide active materials I can be prepared as described in the prior art documents cited.

In general, the procedure will be to obtain, from sources of the catalytically active oxide material I, a very intimate, preferably finely divided, dry mixture of composition corresponding to the stoichiometry of the desired oxide material I (a precursor material), and to calcine (thermally treat) it at temperatures of 300 to 600-° C., preferably 400 to 550-° C. The calcination can be performed either under inert gas or under an oxidative atmosphere, for example air (or another mixture of inert gas and oxygen), or else under a reducing atmosphere (for example a mixture of inert gas and reducing gases such as $NH_3$ and CO). The calcination time will generally be a few hours and typically decreases with the magnitude of the calcination temperature.

Useful sources for the elemental constituents of the mixed oxide active materials I are especially those compounds which are already oxides and/or those compounds which can be converted to oxides by heating, at least in the presence of oxygen. The intimate mixing of the starting compounds (sources) can be effected in dry or in wet form. Where it is effected in dry form, the starting compounds are appropriately used in the form of fine powders and, after mixing and optional compaction, subjected to calcination. However, preference is given to effecting the intimate mixing in wet form. In this case, the starting compounds are typically mixed with one another in the form of aqueous suspensions and/or solutions. Particularly intimate dry mixtures are obtained in the mixing process described when the starting materials are exclusively sources of the elemental constituents present in dissolved form.

The solvent used is preferably water. Preference is given to preparing, from the starting compounds, at least two aqueous solutions, at least one of which is an acidic solution and at least one of which an ammoniacal (basic) solution.

Combination of the aqueous solutions generally results in precipitation reactions in which precursor compounds of the multimetal oxide active material I form.

Subsequently, the aqueous material obtained is dried, and the drying operation can be effected, for example, by spray drying.

The catalytically active oxide material obtained after the calcining of the dry material can be used to charge reaction zone A for the FORMOX process in finely divided form as such, or applied with the aid of a liquid binder to an outer surface of a shaped support body in the form of an eggshell catalyst. However, eggshell catalysts can also be produced by applying, with the aid of a liquid binder, fine precursor powder to the outer surface of shaped support bodies, and calcining the precursor substance only after completion of application and drying.

The multimetal oxide active materials I can, however, also be used in reaction zone A in pure, undiluted form, or diluted with oxidic, essentially inert diluent material, in the form of what are called unsupported catalysts (this is preferred in accordance with the invention). Examples of inert diluent materials suitable in accordance with the invention include finely divided aluminum oxide, silicon dioxide, aluminosilicates, zirconium dioxide, titanium dioxide or mixtures thereof. Undiluted unsupported catalysts are preferred in accordance with the invention.

In the case of shaped unsupported catalyst bodies, the shaping is advantageously effected with precursor powder which is not calcined until after the shaping. The shaping is effected typically with addition of shaping aids, for example graphite (lubricant) or mineral fibers (reinforcing aid). Suitable shaping processes are tableting and extrusion. It will be appreciated that the shaping may, however, also be performed, for example, with a mixture of active material powder and precursor powder, to which shaping aids and optionally inert diluent powders are again added prior to the shaping. Shaping is followed by another calcination. In principle, the shaping to unsupported catalysts can also be performed only with already prefabricated active material powder and optionally the aids mentioned. This procedure is less advantageous. The shaping here too is generally followed by another calcination.

A favorable Mo source is, for example, ammonium heptamolybdate tetrahydrate $(NH_4)_6 (Mo_7O_{24}) \cdot 4H_2O$. Advantageous iron sources are, for example, iron(III) nitrate [Fe$(NO_3)_3$], iron(III) chloride [$FeCl_3$] or hydrates of iron(III) nitrate, for example $Fe(NO_3)_3 \cdot 9 H_2O$.

Preferred geometries of the shaped support bodies for eggshell catalysts of the mixed oxide active materials I are spheres and rings, the longest dimension of which is 1 to 10 mm, frequently 2 to 8 mm or 3 to 6 mm (the longest dimension of a shaped body in this document is generally understood to mean the longest direct line connecting two points on the surface of the shaped body).

Ring geometries favorable in accordance with the invention have hollow cylindrical shaped support bodies with a length of 2 to 10 mm, an external diameter of 4 to 10 mm and a wall thickness of 1 to 4 mm. The hollow cylindrical shaped support bodies preferably have a length of 3 to 6 mm, an external diameter of 4 to 8 mm and a wall thickness of 1 to 2 mm. In principle, the shaped support bodies may also have an irregular shape.

Suitable materials for the inert shaped support bodies are, for example, quartz, silica glass, sintered silica, sintered or fused alumina, porcelain, sintered or fused silicates such as aluminum silicate, magnesium silicate, zinc silicate, zirconium silicate, and especially steatite (e.g. C 220 steatite from CeramTec).

The inert shaped support bodies differ from the catalytic active material (in this document, "catalytically active material" is quite generally also used as a synonym thereof) normally in that they have a much lower specific surface area. In general, the specific surface area thereof is less than 3 $m^2/g$ of shaped support body. At this point, it should be emphasized that all figures in this document for specific surface areas relate to determinations according to DIN 66131 (determination of specific surface area of solids by means of gas absorption ($N_2$) according to Brunauer-Emmett-Teller (BET)).

The coating of the inert shaped support bodies with the particular finely divided powder is generally executed in a suitable rotatable vessel, for example in a coating drum. Appropriately in application terms, the liquid binder is sprayed onto the inert shaped support bodies and the binder-moistened surface of the shaped support bodies being moved within the coating drum is dusted with the particular powder (cf., for example, EP-A 714700). Subsequently, the adhering liquid is generally removed at least partly from the coated shaped support body (for example by passing hot gas through the coated shaped support bodies, as described in WO 2006/094765). In principle, however, it is also possible to employ all other application processes acknowledged as prior art in EP-A 714700 to produce the relevant eggshell catalysts. Useful liquid binders include, for example, water and aqueous solutions (for example of glycerol in water). For example, the coating of the shaped support bodies can also be undertaken by spraying a suspension of the pulverant material to be applied in liquid binder (for example water) onto the surface of the inert shaped support bodies (generally under the action of heat and a drying entraining gas). In principle, the coating can also be undertaken in a fluidized bed system or powder coating system.

The thickness of the eggshell of catalytically active oxide material applied to the surface of the inert shaped support body is, in the case of the mixed oxide active materials I, appropriately in application terms, generally 10 to 1000 µm. The eggshell thickness is preferably 10 to 500 µm, more preferably 100 to 500 µm and most preferably 200 to 300 µm. Beyond the statements already made, suitable ring geometries for possible inert shaped support bodies of annular eggshell oxidation catalysts A for the inventive purposes in reaction zone A are all ring geometries disclosed in DE-A 102010028328 and in DE-A 102010023312, and all disclosed in EP-A 714700.

Preferred shaped unsupported catalyst bodies comprising mixed oxide active materials I are solid cylinders, hollow cylinders and trilobes. The external diameter of cylindrical unsupported catalysts is, appropriately in application terms, 3 to 10 mm, preferably 4 to 8 mm and in particular 5 to 7 mm.

The height thereof is advantageously 1 to 10 mm, preferably 2 to 6 mm and in particular 3 to 5 mm. The same applies in the case of hollow cylinders. In addition, the internal diameter of the orifice running through from the top downward is advantageously 1 to 8 mm, preferably 2 to 6 mm and most preferably 2 to 4 mm. Appropriately in application terms, the wall thickness of hollow cylinders is 1 to 3 mm.

In the case of shaped unsupported catalyst bodies (unsupported catalysts), the shaping can be effected, for example, in such a way that the pulverant active material or the uncalcined precursor material thereof (the latter being preferred in accordance with the invention) is used to directly produce unsupported catalysts or unsupported catalyst precursors by compaction (for example by tableting or extrusion) to the desired catalyst geometry, the shaping optionally being preceded by addition of assistants, for example graphite or stearic acid as lubricants, and/or shaping assistants and reinforcing assistants such as microfibers of glass, asbestos, silicon carbide or potassium titanate. In the case of annular geometries, the tableting can advantageously be undertaken as described in documents WO 2008/152079, WO 2008/087116, DE-A 102008040094, DE-A 102008040093 and WO 2010/000720. All geometries detailed in the aforementioned documents are also suitable for inventive unsupported oxidation catalysts A.

Mixed oxide active material I oxidation catalysts A can, however, also be employed in reaction zone A as supported catalysts. In contrast to shaped support bodies for the eggshell oxidation catalysts A, which are preferably nonporous or low in pores, in the case of supported catalysts A, the active material is introduced into the pore structure of the shaped support bodies. In this case, the starting materials are therefore comparatively porous shaped support bodies which, for example, are impregnated successively with the at least two solutions of the precursor compounds. The precipitation reaction described proceeds in the pores of the shaped support body, and the precursor compounds which form therein can subsequently be converted to the desired mixed oxide active material I by calcination. Alternatively, it is also possible to impregnate with a solution comprising all sources required in dissolved form, to dry and then to calcine (cf., for example, DE-A 2442311). Otherwise, the procedure for preparation of the mixed oxide active material I oxidation catalysts may be as in the prior art documents to which reference is made in this regard in this application.

These are especially documents U.S. Pat. Nos. 3,716,497, 3,846,341, EP-A 199359, DE-A 2145851, U.S. Pat. No. 3,983,073, DE-A 2533209, EP-A 2213370 and Catalysis Review, 47, pages 125-174 (2004).

It will be appreciated that, in the FORMOX process too, it is not only possible to use comparatively pure methanol to obtain reaction gas input mixture A. Methanol raw materials suitable in this regard in accordance with the invention are also aqueous methanol solutions and technical-grade methanol, which can be used after appropriate evaporation to obtain reaction gas input mixture A.

It is also possible to charge reaction zone A with a fixed catalyst bed which comprises FORMOX oxidation catalysts A in a form diluted with inert shaped bodies.

The space velocity on the fixed catalyst bed present in reaction zone A of reaction gas input mixture A will, in the case of a FORMOX process employed in accordance with the invention, generally be 3500 l (STP)/l.h to 75 000 l (STP)/l.h, preferably 25 000 l (STP)/l.h to 35 000 l (STP)/l.h. The term "space velocity" is used as defined in DE-A 19927624.

Suitable reactors for execution of the FORMOX process in reaction zone A are especially also the heat exchanger reactors which have already been recommended for implementation of reaction zone A in the case of the silver process (cf., for example, WO 2005/063375).

In accordance with the invention, the FORMOX process is also preferred in reaction zone A because the product gas mixture A thereof, in contrast to a product gas mixture A after the silver process, is free of molecular hydrogen.

In other words, the product gas mixture A of a heterogeneously catalyzed partial gas phase oxidation of methanol to formaldehyde after the FORMOX process is (without subjecting it to a removal process beforehand, without performing a removal process thereon beforehand) the ideal formaldehyde source for formaldehyde required in reaction gas input mixture B.

Frequently, product gas mixture A is obtained in the FORMOX process with a temperature with which it can be used without further thermal pretreatment for production of reaction gas input mixture B. In many cases, the temperature of the product gas mixture A leaving reaction zone A, both in the case of the silver process and in the case of the FORMOX process, however, is different from that temperature with which it is to be used to obtain reaction gas input mixture B. Against this background, the stream of product gas mixture A, on its way from reaction zone A into reaction zone B, can flow through an indirect heat exchanger in order to match its temperature to the addition temperature envisaged for production of reaction gas input mixture B.

For the sake of completeness, it should also be added that, in the case of employment of the FORMOX process in reaction zone A too, the stream Z obtained in separation zone T in the process according to the invention constitutes a suitable inert gas source for the inert gas required in reaction gas input mixture A and, appropriately in application terms, a substream of stream Z is recycled into reaction zone A to obtain reaction gas input mixture A.

A useful source for the acetic acid required in reaction gas input mixture B for the process according to the invention is especially the carbonylation of methanol in the liquid phase:

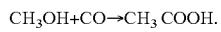

$$CH_3OH + CO \rightarrow CH_3COOH.$$

The reaction is performed with a catalyst (homogeneous catalysis). Typically, the catalyst comprises at least one of the elements Fe, Co, Ni, Ru, Rh, Pd, Cu, Os, Ir and Pt, an ionic halide (e.g. KI) and/or a covalent halide (e.g. $CH_3I$) as a promoter (the iodides normally being the preferred promoters), and optionally a ligand, for example $PR_3$ or $NR_3$ where R is an organic radical. Corresponding carbonylation processes are disclosed, for example, in documents EP-A 1506151, DE 3889233 T2, EP-A 277824, EP-A 656811, DE-A 1941449, U.S. Pat. No. 6,420,304, EP-A 161874, U.S. Pat. No. 3,769,329, EP-A 55618, EP-A 87870, U.S. Pat. Nos. 5,001,259, 5,466,874 and U.S. Pat. No. 502698, and the prior art cited in these documents. The working conditions require high pressures (at least 3 MPa (abs.)) and elevated temperatures (at least 150° C. or 250° C.). The catalyst system currently being employed preferentially in industrial scale processes is Rh in combination with $HI/CH_3I$ as the promoter system (cf. DE 68916718 T2 and U.S. Pat. No. 3,769,329). The selectivities of acetic acid formation achieved, based on methanol converted, are ≥99 mol % (Industrielle Organische Chemie, Klaus Weissermel and Hans-Jürgen Arpe, Wiley-VCH, 5th edition, 1998, page 196 and Ullmann's Encyclopedia of Industrial Chemistry, Sixth Edition, volume 6 (2003), pages 467 to 491).

Since the liquid phase carbonylation of methanol, as described above, requires the additional use of halide promoters which have strongly corrosive action and require the use of expensive corrosion-resistant construction materials, the acetic acid formed is removed by rectification from the product mixture obtained in the carbonylation of methanol for use in the process according to the invention. This is typically accomplished in a purity of acetic acid content of at least 99.8% by weight (cf. Industrielle Organische Chemie, Klaus Weissermel and Hans-Jürgen Arpe, Wiley-VCH, 5th edition, 1998, page 196).

By conversion of such acetic acid removed by rectification to the gas phase (vapor phase) and combination with product gas mixture A or product gas mixture A*, it is possible in accordance with the invention, in a comparatively simple manner, to obtain the reaction gas input mixture B required for reaction zone B.

In principle, the carbonylation of methanol to acetic acid in the liquid phase can also be performed with exclusion of halide-comprising promoters (cf., for example, DE-A 3606169). In this case, the acetic acid present in the crude product of the carbonylation of methanol need not necessarily be removed by rectification therefrom in order to be able to be employed for production of reaction gas input mixture B. Instead, in this case, the crude product can also be converted as such to the vapor phase and used to obtain reaction gas input mixture B.

In a particularly skillful manner in accordance with the invention, the carbonylation of methanol with carbon monoxide will, however, be performed in the gas phase, and the resulting product gas mixture comprising the acetic acid formed will be used directly to obtain reaction gas input mixture B.

Particularly advantageously, heterogeneously catalyzed gas phase carbonylation processes of methanol to acetic acid will be employed, which do not require presence of halogen-containing promoters. Corresponding gas phase carbonylations of methanol to acetic acid are disclosed by U.S. Pat. No. 4,612,387 and EP-A 596632. A characteristic feature of these processes is that the catalysts employed are zeolites (aluminosilicates) with anionic structural charge, which preferably have, on their inner and/or outer surfaces, at least one cation type from the group of the cations of the elements copper, iridium, nickel, rhodium and cobalt, in order to balance out (to neutralize) the negative structural charge. Particularly advantageous zeolites are those which have a mordenite structure (cf. Studies in Surface, Science and Catalysis, vol. 101, 11th International Congress on Catalysis—40th Anniversary), 1996, Elsevier, Science B. V., Lausanne, pages 771 to 779).

It will be appreciated that the acetic acid source (the raw material) used for reaction gas input mixture B may also be an aqueous acetic acid solution or technical-grade acetic acid solution, which can be used after appropriate evaporation to obtain reaction gas input mixture B.

Reaction gas input mixture B can be obtained from the stream of product gas mixture A leaving reaction zone A, or the stream of product gas mixture A* leaving separation zone T*, and the acetic acid source converted to the vapor phase as at least one further stream, and stream Y, and optionally further streams, for example additional steam or additional inert diluent gas other than steam (also referred to in this document merely as inert gas for short). If required, for example when product gas mixture A does not comprise any excess molecular oxygen, reaction gas input mixture B can also be produced with additional use of molecular oxygen or a mixture of inert gas and molecular oxygen, since a low (limited) oxygen content in reaction gas input mixture B generally has an advantageous effect on the service life of aldol condensation catalyst B.

The temperature of reaction gas mixture B in the process according to the invention within reaction zone B will normally be within the range from 260 to 400° C., preferably within the range from 270 to 390° C., more preferably within the range of 280 to 380° C., advantageously within the range of 300 to 370° C. and particularly advantageously within the range of 300 to 340° C.

The term "temperature of reaction gas mixture B" (also referred to in this document as reaction temperature in reaction zone B) means primarily that temperature that reaction gas mixture B has from attainment of a conversion of the formaldehyde present in reaction gas input mixture B of at least 5 mol % until attainment of the appropriate final conversion of the formaldehyde within reaction zone B. Advantageously in accordance with the invention, the temperature of reaction gas mixture B over the entire reaction zone B is within the aforementioned temperature ranges. Advantageously, reaction gas input mixture B is already supplied to reaction zone B with a temperature within the range from 260 to 400° C. Frequently, however, a charge of reaction zone B with solid inert material or of catalytically active catalyst charge highly diluted with such inert material is present at the inlet into reaction zone B in flow direction upstream of the actual catalytically active catalyst charge of reaction zone B. As it flows through such a primary charge of reaction zone B, the temperature of the reaction gas input mixture B supplied to reaction zone B can be adjusted in a comparatively simple manner to the value with which reaction gas mixture B is to enter the actual catalytically active catalyst charge of reaction zone B. In general, the temperature of the product gas mixture A leaving reaction zone A is different than this temperature. Against this background, the stream of product gas mixture A, on its way from reaction zone A into reaction zone B, can flow through an indirect heat exchanger in order to approximate its temperature to the inlet temperature envisaged for reaction gas input mixture B into reaction zone B, or to bring it to this temperature.

In principle, the charge of reaction zone B with at least one aldol condensation catalyst B can be configured as a fluidized bed. Advantageously in application terms, the charge of reaction zone B with aldol condensation catalyst B is, however, configured as a fixed bed.

With regard to the working pressure which exists in reaction zone B, the same applies correspondingly as has already been stated for the working pressure which exists in reaction zone A. In general, the working pressure in reaction zone B, due to the pressure drop which occurs as reaction gas mixture A flows through reaction zone A, is lower than the working pressure in reaction zone A. It is also possible to configure reaction zone B in corresponding heat exchanger reactors to reaction zone A, in which case the same rules of preference apply.

The formaldehyde content in reaction gas input mixture B will, in the process according to the invention, generally be 0.5 to 10% by volume, preferably 0.5 to 7% by volume and more preferably 1 to 5% by volume.

The ratio $n_{HAc}:n_{Fd}$ of molar amount of acetic acid present in reaction gas input mixture B ($n_{HAc}$) to molar amount of formaldehyde present therein ($n_{Fd}$) in the process according to the invention is greater than 1 and may be up to 10 ($n_{Fd}$ is understood to mean the sum of formaldehyde units present in monomeric form (preferred) and possibly in oligomeric and polymeric form (formaldehyde has a tendency to such formations) in reaction gas input mixture B, since the latter undergo redissociation to monomeric formaldehyde under the reaction conditions in reaction zone B). Advantageously in accordance with the invention, the ratio $n_{HAc}:n_{Fd}$ in reaction gas input mixture B is 1.1 to 5 and more preferably 1.5 to 3.5. Frequently, the acetic acid content of reaction gas input mixture B will vary within the range from 1 or from 1.5 to 20% by volume, advantageously within the range from 2 to 15% by volume and particularly advantageously within the range from 3 to 10% by volume. The molecular oxygen content of reaction gas input mixture B varies, in the process according to the invention, appropriately in application terms, within the range from 0.5 to 5% by volume, preferably within the range from 1 to 5% by volume and more preferably within the range from 2 or from 3 to 5% by volume. Presence of molecular oxygen in reaction gas input mixture B has an advantageous effect on the service life of the catalyst charge of reaction zone B. When the oxygen content of reaction gas mixture B is too high, however, there is unwanted carbon oxide formation in reaction zone B. In principle, the molecular oxygen content in reaction gas input mixture B in the process according to the invention may, however, also be vanishingly small.

The steam content of reaction gas input mixture B in the process according to the invention should not exceed 30% by volume since presence of steam in reaction gas mixture B has an unfavorable effect on the equilibrium position of the aldol condensation. Appropriately in application terms, the steam content of reaction gas input mixture B will therefore generally not exceed 25% by volume and preferably 20% by volume. In general, the steam content of reaction gas input mixture B will be at least 0.5% or at least 1% by volume. Advantageously, the steam content of reaction gas input mixture B is 0.5 to 15% by volume and, taking account of the effect thereof and formation thereof in reaction zone A, in particular 1 to 10% by volume. The proportion by volume of inert diluent gases other than steam in reaction gas input mixture B will normally be at least 30% by volume. Preferably, the aforementioned inert gas content is at least 40% by volume or at least 50% by volume. In general, the proportion of inert diluent gas other than steam in reaction gas input mixture B will not exceed 95% by volume or usually 90% by volume. Particularly advantageously in application terms, reaction gas input mixture B comprises 60 to 90% by volume, particularly advantageously 70 to 80% by volume, of inert diluent gas other than steam. An inert diluent gas other than steam which is preferred in accordance with the invention is also, in reaction gas input mixture B, molecular nitrogen ($N_2$).

Thus, the molecular nitrogen content of reaction gas input mixture B may be at least 30% by volume, preferably at least 40% by volume or at least 50% by volume. In general, reaction gas input mixture B comprises not more than 95% by volume and usually not more than 90% by volume of molecular nitrogen. Advantageously, reaction gas input mixture B comprises 60 to 90% by volume, particularly advantageously 70 to 80% by volume, of molecular nitrogen.

Useful catalysts for charging of reaction zone B include, for example, those disclosed in I & EC PRODUCT RESEARCH AND DEVELOPMENT, vol. 5, No. 1, March 1966, pages 50 to 53. This group of basic catalysts comprises firstly zeolites (aluminosilicates) with anionic structural charge, on the inner and outer surfaces of which at least one cation type from the group of the alkali metal ions and alkaline earth metal ions is present (preferably $Na^+$, $K^+$, $Ca^{2+}$ and/or $Mg^{2+}$), in order to balance out (to neutralize) the negative structural charge. However, it also comprises hydroxide applied to inert supports (e.g. amorphous silicon dioxide (silica gel)), from the group consisting of alkali metal hydroxides, alkaline earth metal hydroxides and aluminum hydroxide (preferably KOH, NaOH, $Ca(OH)_2$ and $Mg(OH)_2$).

However, also suitable for charging reaction zone B are the acidic catalysts disclosed in EP-A 164614.

These are catalysts which comprise as constituent a), at least one oxide of at least one of the elements Si, Al, Ti, Zr, Cd, Sn, Ga, Y and La and/or zeolite, and as constituent b), at least one oxide selected from boron oxide and phosphorus oxide, and optionally as constituent c) one or more than one oxide of at least one of the elements V, Cr, Co, Ni, Mo and Pb and/or one or more than one heteropolyacid with at least one poly atom selected from V, Mo and W.

Preferred boron oxide is $B_2O_3$, and preferred phosphorus oxide is $P_2O_5$.

Preference is given to catalysts whose boron oxide content (calculated as $B_2O_3$ (based on the amount of B present)) is 1 to 50% by weight. However, catalysts favorable in accordance with the invention are also those whose phosphorus oxide content (calculated as $P_2O_5$ (based on the amount of P present)) is 1 to 50% by weight. However, useful aldol condensation catalysts B for the process according to the invention also include those among the aforementioned catalysts whose total content of phosphorus oxide (calculated as $P_2O_5$) and of boron oxide (calculated as $B_2O_3$) is 1 to 50% by weight. The aforementioned contents of phosphorus oxide and/or boron oxide are preferably 5 to 30% by weight.

In addition, constituent a) is preferably at least one oxide of at least one of the elements Si, Al, Ti and Zr.

Particularly favorable in accordance with the invention are the combinations of titanium oxide as constituent a) and boron oxide or phosphorus oxide as constituent b), or silicon dioxide-aluminum oxide as constituent a) and boron oxide as constituent b), or aluminum oxide as constituent a) and boron oxide or phosphorus oxide as constituent b). When the catalysts detailed above additionally comprise a heteropolyacid, it preferably comprises at least one of the elements P, B and Si as a heteroatom. When the aforementioned catalysts comprise a constituent c), the amount thereof is normally 0.01 to 10 mmol per gram of catalyst and in many cases 0.03 to 5 mmol per gram of catalyst. It is favorable when the catalysts have, as constituent c), both at least one of the oxides and at least one of the heteropolyacids.

More preferably in accordance with the invention, reaction zone B is, however, charged with aldol condensation catalysts B whose active material is a vanadium-phosphorus oxide and/or a vanadium-phosphorus oxide doped with elements other than vanadium and phosphorus (also referred to collectively in the literature as V-P-O catalysts).

Such catalysts have been described before in the literature and are recommended there especially as catalysts for the heterogeneously catalyzed partial gas phase oxidation of hydrocarbons having at least four carbon atoms (especially n-butane, n-butene and/or benzene) to maleic anhydride.

Surprisingly, these catalysts known from the prior art for aforementioned partial oxidations are suitable in principle as aldol condensation catalysts B for charging reaction zone B. They are notable for particularly high selectivities of target product formation (of acrylic acid formation) (with simultaneously high formaldehyde conversions).

Accordingly, the aldol condensation catalysts B used in the process according to the invention may, for example, be all of those disclosed in documents U.S. Pat. Nos. 5,275,996, 5,641,722, 5,137,860, 5,095,125, DE-69702728 T2, WO 2007/012620, WO 2010/072721, WO 2001/68245, U.S. Pat. No. 4,933,312, WO 2003/078310, Journal of Catalysis 107, pages 201-208 (1987), DE-A 102008040094, WO 97/12674, "Neuartige Vanadium (IV)-phosphate fur die Partialoxidation von kurzkettigen Kohlenwasserstoffen-Synthesen, Kristallstrukturen, Redox-Verhalten und katalytische Eigenschaften [Novel vanadium(IV) phosphates for the partial oxidation of short-chain hydrocarbon syntheses, crystal structures, redox behavior and catalytic properties], thesis by Ernst Benser, 2007, Rheinische Friedrichs-Wilhelms-Universität Bonn", WO 2010/072723, "Untersuchung von V-P-O-Katalysatoren für die partielle Oxidation von Propan zu Acrylsäure [Study of V-P-O catalysts for the partial oxidation of propane to acrylic acid], thesis by Thomas Quandt, 1999, Ruhr-Universität Bochum", WO 2010/000720, WO 2008/152079, WO 2008/087116, DE-A 102008040093, DE-A 102005035978 and DE-A 102007005602, and the prior art acknowledged in these documents. In particular, this applies to all exemplary embodiments of the above prior art, especially those of WO 2007/012620.

The phosphorus/vanadium atomic ratio in the undoped or doped vanadium-phosphorus oxides is, advantageously in accordance with the invention, 0.9 to 2.0, preferably 0.9 to 1.5, more preferably 0.9 to 1.2 and most preferably 1.0 to 1.1. The arithmetic mean oxidation state of the vanadium therein is preferably +3.9 to +4.4 and more preferably 4.0 to 4.3. These active materials also advantageously have a specific BET surface area of $\geq 15$ m$^2$/g, preferably of $\geq 15$ to 50 m$^2$/g and most preferably of $\geq 15$ to 40 m$^2$/g. They advantageously have a total pore volume of $\geq 0.1$ ml/g, preferably of 0.15 to 0.5 ml/g and most preferably of 0.15 to 0.4 ml/g. Total pore volume data in this document relate to determinations by the method of mercury porosimetry using the Auto Pore 9220 test instrument from Micromeritics GmbH, DE-4040 Neuss (range from 30 Angstrom to 0.3 mm). As already stated, the vanadium-phosphorus oxide active materials may be doped with promoter elements other than vanadium and phosphorus. Useful such promoter elements include the elements of groups 1 to 15 of the Periodic Table other than P and V. Doped vanadium-phosphorus oxides are disclosed, for example, by WO 97/12674, WO 95/26817, U.S. Pat. Nos. 5,137,860, 5,296,436, 5,158,923, 4,795,818 and WO 2007/012620.

Promoters preferred in accordance with the invention are the elements lithium, potassium, sodium, rubidium, cesium, thallium, molybdenum, zinc, hafnium, zirconium, titanium, chromium, manganese, nickel, copper, iron, boron, silicon, tin, niobium, cobalt and bismuth, among which preference is given not only to iron but especially to niobium, molybdenum, zinc and bismuth. The vanadium-phosphorus oxide active materials may comprise one or more promoter elements. The total content of promoters in the catalytic active material is, based on the weight thereof, generally not more than 5% by weight (the individual promoter element calculated in each case as the electrically uncharged oxide in which the promoter element has the same charge number (oxidation number) as in the active material).

Useful active materials for aldol condensation catalysts B for charging reaction zone B are thus especially multielement oxide active materials of the general formula II

$$V_1P_bFe_cX^1_dX^2_eO_n \qquad (II),$$

in which the variables are each defined as follows:
$X^1$=Mo, Bi, Co, Ni, Si, Zn, Hf, Zr, Ti, Cr, Mn, Cu, B, Sn and/or Nb, preferably Nb, Mo, Zn and/or Hf,
$X^2$=Li, K, Na, Rb, Cs and/or Tl,
b=0.9 to 2.0, preferably 0.9 to 1.5, more preferably 0.9 to 1.2 and most preferably 1.0 to 1.1,
c=$\geq$0 to 0.1,
d=$\geq$0 to 0.1,
e=$\geq$0 to 0.1, and
n=the stoichiometric coefficient of the element oxygen, which is determined by the stoichiometric coefficients of the non-oxygen elements and the charge numbers thereof in II.

Irrespective of the stoichiometric coefficients d, e and b, the stoichiometric coefficient c is, advantageously in accordance with the invention, in active materials of the general formula II, 0.005 to 0.1, preferably 0.005 to 0.05 and particularly advantageously, 0.005 to 0.02.

The aldol condensation catalysts B may comprise the multimetal oxide active materials of the general formula II, for example, in pure, undiluted form, or diluted with an oxidic, essentially inert dilution material in the form of unsupported catalysts. Inert dilution materials suitable in accordance with the invention include, for example, finely divided aluminum oxide, silicon dioxide, aluminosilicates, zirconium dioxide, titanium dioxide or mixtures thereof. Undiluted unsupported catalysts are preferred in accordance with the invention. The unsupported catalysts may in principle be of any shape. Preferred shaped unsupported catalyst bodies are spheres, solid cylinders, hollow cylinders and trilobes, the longest dimension of which in all cases is advantageously 1 to 10 mm.

In the case of shaped unsupported catalyst bodies, the shaping is advantageously effected with precursor powder which is calcined only after the shaping. The shaping is effected typically with addition of shaping assistants, for example graphite (lubricant) or mineral fibers (reinforcing aids). Suitable shaping processes are tableting and extrusion.

The external diameter of cylindrical unsupported catalysts is, appropriately in application terms, 3 to 10 mm, preferably 4 to 8 mm and in particular 5 to 7 mm. The height thereof is advantageously 1 to 10 mm, preferably 2 to 6 mm and in particular 3 to 5 mm. The same applies in the case of hollow cylinders. In addition, the internal diameter of the orifice running through from the top downward is advantageously 1 to 8 mm, preferably 2 to 6 mm and most preferably 2 to 4 mm. A wall thickness of 1 to 3 mm is appropriate in application terms in the case of hollow cylinders. It will be appreciated that the doped or undoped vanadium-phosphorus oxide active materials can also be used in powder form, or as eggshell catalysts with an active material eggshell applied to the surface of inert shaped support bodies, as aldol condensation catalysts B in reaction zone B. The preparation of the eggshell catalysts, the eggshell thickness and the geometry of the inert shaped support bodies may be selected as described in the case of the eggshell catalysts for reaction zone A.

Otherwise, doped or undoped vanadium-phosphorus oxide active materials and unsupported catalysts manufactured therefrom can be produced as described in the documents of the prior art, to which reference is made in this patent application.

These are especially the documents WO 2007/012620, WO 2010/07273, WO 2010/000720 and WO 2010/000764.

For example, the procedure may be as follows:
a) reaction of a pentavalent vanadium compound (e.g. $V_2O_5$) with an organic reducing solvent (e.g. isobutanol) in the presence of a pentavalent phosphorus compound (e.g. ortho- and/or pyrophosphoric acid) with heating to 75 to 205° C., preferably to 100 to 120° C.;
b) cooling of the reaction mixture to advantageously 40 to 90° C.;
c) optional addition of compounds comprising doping elements, for example iron(III) phosphate;
d) reheating to 75 to 205° C., preferably 100 to 120° C.;
e) isolation of the solid precursor material formed, comprising V, P, O and, for example, Fe (for example by filtering);
f) drying and/or thermal pretreatment of the precursor material (optionally until commencement of preforming by elimination of water from the precursor material);
g) addition of shaping aids, for example finely divided graphite or mineral fibers, and subsequent shaping to give the shaped unsupported catalyst precursor body by, for example, tableting;
h) subsequent thermal treatment of the shaped catalyst precursor bodies formed by heating in an atmosphere which comprises oxygen, nitrogen, noble gases, carbon dioxide, carbon monoxide and/or steam (for example as described in WO 2003/078310 at page 20, line 16 to page 21, line 35). The temperature of the thermal treatment generally exceeds 250° C., in many cases 300° C. or 350° C., but normally not 600° C., preferably not 550° C. and most preferably not 500° C.

The space velocity of the catalyst charge on reaction zone B of formaldehyde present in reaction gas input mixture B may, in accordance with the invention, be 1 to 100, preferably 2 to 50 and more preferably 3 to 30 or 4 to 10 l(STP)/l.h. The term "space velocity" is used as defined in DE-A 19927624. Both in reaction zone A and in reaction zone B, the particular fixed catalyst bed may consist only of catalysts comprising active material, or else of a mixture of catalysts comprising active material and inert shaped bodies.

Especially in the case of use of V-P-O catalysts as aldol condensation catalysts in reaction zone B, in the process according to the invention, based on a single pass of reaction gas mixture B through reaction zone B, at least 95 mol %, usually at least 98 mol %, of the formaldehyde present in reaction gas input mixture B is converted. The selectivity of acrylic acid formation, based on formaldehyde converted, is generally ≥95 mol %, frequently ≥98 mol %.

Suitable in accordance with the invention for configuration of reaction zone B are those heat exchanger reactors which have already been recommended for implementation of reaction zone A.

The product gas mixture B which leaves reaction zone B and which comprises acrylic acid formed, unconverted acetic acid, at least one inert diluent gas other than steam, and steam, with or without (and optionally) molecular oxygen, can be separated in a manner known per se into the at least three streams X, Y and Z in a separation zone T.

For example, the separation can be effected by fractional condensation, as recommended in documents DE-A 102007004960, DE-A 10 2007055086, DE-A 10243625, DE-A 10235847 and DE-A 19924532. In this procedure, the temperature of product gas mixture B is optionally first reduced by direct and/or indirect cooling, and product gas mixture B is then passed into a condensation column equipped with separating internals (for example mass transfer trays) and optionally provided with cooling circuits, and fractionally condensed ascending into itself within the condensation column. Appropriate selection of the number of theoretical plates in the condensation column allows streams X, Y and Z to be conducted out of the condensation column as separate fractions with the desired degree of enrichment in each case.

Appropriately in application terms, stream X is generally removed with an acrylic acid content of ≥90% by weight, preferably ≥95% by weight, and conducted out of the condensation column. In the event of an increased purity requirement, stream X can, advantageously in application terms, be purified further by crystallization (preferably suspension crystallization) (cf. the aforementioned prior art documents and WO 01/77056). It will be appreciated that the stream X conducted out of the condensation column can also be purified further by rectification. It is possible in both ways, with a comparatively low level of complexity, to achieve acrylic acid purities of ≥99.9% by weight, which are suitable for production of water-absorbing resins by free-radical polymerization of monomer mixtures comprising acrylic acid and/or the sodium salt thereof.

The water-absorbing resins can be prepared, for example, as described in documents WO 2008/116840, DE-A 102005062929, DE-A 102004057874, DE-A 102004057868, DE-A 102004004496 and DE-A 19854575.

In a corresponding manner, stream Y is normally also conducted out of the condensation column with an acetic acid content of ≥90% by weight, preferably ≥95% by weight. The stream Y thus removed can be recycled as such into reaction zone B to obtain reaction gas input mixture B. It will be appreciated that it is also possible, prior to the recycling of the stream Y removed as described into reaction zone B, to further enrich the acetic acid content thereof by rectificative and/or crystallizative means (for example to acetic acid contents of ≥99% by weight), or to remove stream Y in the condensation column directly with such elevated purity by increasing the number of theoretical plates therein. Stream Z normally leaves the condensation column overhead.

Alternatively, it is also possible to proceed as recommended in documents DE-A 102009027401 and DE-A 10336386. After optional preceding direct and/or indirect cooling, product gas mixture B in this procedure, in an absorption column advantageously equipped with separating internals, is conducted in countercurrent to an organic solvent having a higher boiling point than acrylic acid at standard pressure ($10^5$ Pa) (useful examples of these are the organic solvents specified in DE-A 102009027401 and in DE-A 10336386), and the acetic acid and acrylic acid present in product gas mixture B are absorbed into the organic solvent, while a stream Z leaves the adsorption column at the top thereof. From the absorbate comprising acetic acid and acrylic acid, it is possible to remove streams X and Y with the desired degree of enrichment in each case by rectification (fractional distillation) in a rectification column in a manner known per se through appropriate selection of the number of theoretical plates. In general, this degree of enrichment of acrylic acid or acetic acid will be at least 90% by weight, preferably at least 95% by weight. A subsequent crystallizative further purification of the stream X removed (for example as disclosed in WO 01/77056) leads with a comparatively low level of complexity to acrylic acid purities of ≥99.9% by weight, which are suitable for production of water-absorbing resins by free-radical polymerization of monomer mixtures comprising acrylic acid and/or the sodium salt thereof. The stream Y removed by rectification as described can be recycled as such, or after optional crystallizative and/or rectificative further purification (for example to acetic acid contents of ≥99% by weight) into reaction zone B to obtain reaction gas input mixture B. By appropriately increasing the number of theoretical plates, it is also possible to remove stream Y from the absorbate by rectification directly with such a degree of enrichment.

Instead of using an organic absorbent, following the teaching of EP-A 551111 or EP-A 778255, it is also possible to absorb the acrylic acid and acetic acid present in product gas mixture B therefrom into an aqueous absorbent in an absorption column, while a stream Z leaves the absorption column at the top thereof. Subsequent rectificative separation of the aqueous absorbent, with optional inclusion of an azeotropic entraining agent, gives the desired streams X and Y.

The conversion of the acetic acid and acrylic acid present in reaction gas mixture B to the condensed phase to leave a gaseous stream Z can also be effected, for example, by one-stage condensation of those constituents present in reaction gas mixture B whose boiling points at standard pressure are not above that of acetic acid. Subsequently, the condensate comprising acrylic acid and acetic acid can be separated again, in the degree of enrichment desired in each case, into at least one stream Y and at least one stream X.

Appropriately in application terms, in the process according to the invention, at least 90 mol %, preferably at least 95 mol %, more preferably at least 98 mol % or at least 99 mol % of the acetic acid present in product gas mixture B is recycled into reaction zone B to obtain reaction gas input mixture B.

Instead of the process according to the invention being followed by a process in which acrylic acid present in stream X or a mixture of acrylic acid present in stream X and one or more at least monoethylenically unsaturated monomers other than acrylic acid are polymerized to polymers (for example by free-radical means; the polymerization may, for example, be a solution polymerization or an aqueous emulsion polymerization or a suspension polymerization), the process according to the invention may also be followed by a process in which acrylic acid present in stream X is esterified with at least one alcohol having, for example, 1 to 8 carbon atoms (for example an alkanol such as methanol, ethanol, n-butanol, tert-butanol and 2-ethylhexanol) to give the corresponding acrylic esters (acrylate). The process for acrylic ester preparation may then again be followed by a process in which the acrylic ester prepared or a mixture of the acrylic ester prepared and one or more at least monoethylenically unsaturated monomers other than the acrylic ester prepared are polymerized to polymers (for example by free-radical means; the polymerization may, for example, be a solution polymerization or an aqueous emulsion polymerization or a suspension polymerization).

For the sake of good order, it should also be emphasized that deactivation of the different catalysts in the different reaction zones of the process according to the invention can be counteracted by correspondingly increasing the reaction temperature in the particular reaction zone (in order to keep the reactant conversion based on a single pass of the reaction gas mixture through the catalyst charge stable). It is also possible to regenerate the oxidic active materials of reaction zones A and B in a manner corresponding to that described for comparable oxidic catalysts in WO 2005/042459, by passing over an oxidizing oxygen-comprising gas at elevated temperature.

Reliable operation, especially in reaction zone A, can be ensured in the process according to the invention by an analogous application of the procedure described in WO 2004/007405.

The process according to the invention is notable firstly for its broad and wide-ranging raw material basis in terms of time. Secondly, it is a process which, in contrast to the prior art processes, enables a smooth transition from "fossil acrylic acid" to "renewable acrylic acid" while maintaining the procedure.

"Fossil acrylic acid" is understood to mean acrylic acid for which the ratio of the molar amount of $^{14}C$ atomic nuclei present in this acrylic acid to the molar amount of $^{12}C$ atomic nuclei present in the same acrylic acid, $n^{14}C:n^{12}C$, is vanishingly small.

"Renewable acrylic acid" is understood to mean acrylic acid for which the $n^{14}C:n^{12}C$ ratio corresponds to the ratio V* of $n^{14}C:n^{12}C$ present in the $CO_2$ in the earth's atmosphere, the $n^{14}C:n^{12}C$ ratio being determined by the procedure developed by Willard Frank Libby (http://de.wikipedia.orgn/wiki/Radikohlenstoffdatierung).

The terms "renewable carbon" and "fossil carbon" are used correspondingly in this document.

The process developed by Libby is based on the fact that, compared to the two carbon atom nuclei $^{12}C$ and $^{13}C$, the third naturally occurring carbon nucleus $^{14}C$ is unstable and is therefore also referred to as radiocarbon (half-life=approx. 5700 years).

In the upper layers of the earth's atmosphere, $^{14}C$ is constantly being newly formed by nuclei reaction. At the same time, $^{14}C$ decomposes with a half-life of 5700 years by β-decomposition. An equilibrium forms in the earth's atmosphere between constant new formation and constant degradation, and so the proportion of the $^{14}C$ nuclei in the carbon in the atmosphere on earth is constant over long periods; a stable ratio V* is present in the earth's atmosphere.

The radiocarbon produced in the atmosphere combines with atmospheric oxygen to give $CO_2$, which then gets into the biosphere as a result of photosynthesis. Since life forms (plants, animals, humans), in the course of their metabolism, constantly exchange carbon with the atmosphere surrounding them in this way, the same distribution ratio of the three carbon isotopes and hence the same $n^{14}C:n^{12}C$ ratio is established in living organisms as is present in the surrounding atmosphere.

When this exchange is stopped at the time of death of the life form, the ratio between $^{14}C$ and $^{12}C$ in the dead organism changes because the decomposing $^{14}C$ atomic nucleic are no longer replaced by new ones (the carbon present in the dead organism becomes fossil).

If the death of the organism (life form) was more than 50 000 years ago, the $^{14}C$ content thereof is below the detection limit. Present and future biological ("renewable") raw materials and chemicals produced therefrom have the particular current $^{14}C$ concentration in the CO2 in the atmosphere on the earth (this $n^{14}C:n^{12}C$ ratio=V*). Fossil carbon sources such as coal, mineral oil or natural gas, however, have already lain "dead" in the earth for several million years, and they therefore, just like chemicals produced therefrom, no longer comprise any $^{14}C$.

When fossil acetic acid (acetic acid obtained from fossil raw materials) and renewable formaldehyde (formaldehyde obtained from methanol obtained from renewable raw materials) are used in the process according to the invention, an acrylic acid is obtained whose $n^{14}C:n^{12}C$ ratio is only (⅓)×V.

When, in the process according to the invention, in contrast, acetic acid obtained from renewable raw materials and formaldehyde obtained from fossil methanol are used, an acrylic acid is obtained whose $n^{14}C:n^{12}C$ ratio=(⅔)×V.

When, in the process according to the invention, both fossil (renewable) acetic acid and fossil (renewable) formaldehyde are used, an acrylic acid is obtained whose $n^{14}C:n^{12}C$ ratio =0 (=V*).

When the possibility of blending renewable and fossil starting materials (raw materials) is additionally considered in the process according to the invention, the manufacturer of acrylic acid, when employing the inventive procedure, is thus able, without altering the preparation process (i.e. with one and the same production plant), in accordance with customer requirements (for example the manufacturer of superabsorbents (=water-absorbing resins)), to adjust the "renewable level" of the acrylic acid to be supplied to this customer (the $n^{14}C:n^{12}C$ ratio desired by the customer for the acrylic acid to be supplied) as required.

By esterifying an acrylic acid for which V=V* with biomethanol or bioethanol, it is possible to obtain acrylic esters whose $n^{14}C$ to $n^{12}C$ ratio is likewise V*.

A further advantage of the inventive procedure is that the target product of reaction zone A does not require removal from product gas mixture A in order to be able to be employed for production of reaction gas input mixture B. This ensures both high economy and an efficient energy balance for the process according to the invention. Furthermore, in the case of condensation of acetic acid with formaldehyde, neither glyoxal nor propionic acid is formed as a by-product, as is necessarily the case for a heterogeneously catalyzed partial oxidation of propylene, propane, acrolein, propionaldehyde and/or glycerol to acrylic acid (vgl. WO 2010/074177).

Furthermore, the process according to the invention ensures a high space-time yield coupled with simultaneously high target product selectivity based on the reactants converted.

Thus, the present application especially comprises the following embodiments of the invention:

1. A process for preparing acrylic acid from methanol and acetic acid, which comprises the following measures:

a stream of a reaction gas input mixture A comprising the methanol and molecular oxygen reactants and at least one inert diluent gas other than steam is conducted through a first reaction zone A charged with at least one oxidation catalyst A and, in the course of passage through reaction zone A, methanol present in the reaction gas input mixture A is oxidized under heterogeneous catalysis to formaldehyde and steam so as to form a product gas mixture A comprising formaldehyde, steam and at least one inert diluent gas other than steam, with or without excess molecular oxygen, and a stream of product gas mixture A leaves reaction zone A, it optionally being possible to supply further molecular oxygen and/or further inert diluent gas to the reaction gas mixture A flowing through reaction zone A on its way through reaction zone A, optionally, the stream of product gas mixture A leaving reaction zone A is fed to a separation zone T* and any unconverted methanol still present in product gas mixture A in separation zone T* is removed from product gas mixture A to leave a formaldehyde-comprising product gas mixture A*, and a stream of product gas mixture A* leaves reaction zone A, a stream of a reaction gas input mixture B which comprises acetic acid, steam, at least one inert diluent gas other than steam and formaldehyde, with or without molecular oxygen, and in which the molar amount $n_{HAc}$ of acetic acid present is greater than the molar amount $n_{Fd}$ of formaldehyde present therein is obtained from the stream of product gas mixture A or from the stream of product gas mixture A* and at least one further stream comprising acetic acid, the stream of reaction gas input mixture B is passed through a second reaction zone B charged with at least one aldol condensation catalyst B and formaldehyde present in reaction gas input mixture B, as it flows through reaction zone B, is condensed with acetic acid present in reaction gas input mixture B under heterogeneous catalysis to give acrylic acid and $H_2O$, so as to form a product gas mixture B comprising acrylic acid, acetic acid, steam and at least one inert diluent gas other than steam, with or without molecular oxygen, and a stream of product gas mixture B leaves reaction zone B, it optionally being possible to supply further molecular oxygen and/or further inert diluent gas to the reaction gas mixture B flowing through reaction zone B on its way through reaction zone B, the stream of product gas mixture B leaving reaction zone B is fed to a separation zone T and separated in separation zone T into at least three streams X, Y and Z, the acrylic acid flow present in stream X being greater than the acrylic acid flow present in streams Y and Z together, the acetic acid flow present in stream Y being greater than the acetic acid flow present in streams X and Z together, the flow of inert diluent gas other than steam present in stream Z being greater than the flow of inert diluent gas other than steam present in streams X and Y together, and stream Y is recycled into reaction zone B and used to obtain reaction gas input mixture B.

2. The process according to embodiment 1, wherein methanol removed in separation zone T* is recycled into reaction zone A to obtain reaction gas input mixture A.

3. The process according to embodiment 1 or 2, wherein the methanol is removed by rectification in separation zone T*.

4. The process according to any of embodiments 1 to 3, wherein the at least one oxidation catalyst A has a catalytically active material which comprises at least elemental silver.

5. The process according to embodiment 4, wherein the purity of the elemental silver is ≥99.7% by weight.

6. The process according to embodiment 4, wherein the purity of the elemental silver is ≥99.9% or ≥99.99% by weight.

7. The process according to any of embodiments 4 to 6, wherein the at least one oxidation catalyst A comprises silver crystals who longest dimension is in the range from 0.1 to 5 mm.

8. The process according to embodiment 7, wherein the silver crystals have been coated with a porous layer of oxidic material of at least one of the elements Al, Si, Zr and Ti, the thickness of which is in the range from 0.3 to 10 µm.

9. The process according to any of embodiments 4 to 8, wherein the methanol content of reaction gas input mixture A is at least 5% by volume.

10. The process according to embodiment 9, wherein the methanol content of reaction gas input mixture A is not more than 60% by volume.

11. The process according to any of embodiments 4 to 8, wherein the methanol content of reaction gas input mixture A is 15 to 50% by volume.

12. The process according to any of embodiments 4 to 8, wherein the methanol content of reaction gas input mixture A is 20 to 40% by volume or 20 to 30% by volume.

13. The process according to any of embodiments 4 to 12, wherein reaction gas input mixture A comprises the molecular oxygen in a molar amount $n_o$ and the methanol in a molar amount $n_{Me}$, and the $n_o$:$n_{Me}$ ratio is less than 1.

14. The process according to embodiment 13, wherein $n_o$:$n_{Me}$ is 0.1 to 0.8 or 0.2 to 0.6.

15. The process according to any of embodiments 4 to 14, wherein $n_o$:$n_{Me}$ is 0.3 to 0.5.

16. The process according to any of embodiments 4 to 15, wherein reaction gas input mixture A comprises ≥0 to 50% by volume of $H_2O$.

17. The process according to embodiment 16, wherein reaction gas input mixture A comprises 15 to 35% by volume or 20 to 30% by volume of $H_2O$.

18. The process according to any of embodiments 4 to 17, wherein reaction gas input mixture A comprises $N_2$ as at least one inert diluent gas other than steam.

19. The process according to embodiment 18, wherein reaction gas input mixture A comprises 20 to 80% by volume of $N_2$.

20. The process according to embodiment 18 or 19, wherein reaction gas input mixture A comprises 30 to 70% by volume of $N_2$.

21. The process according to any of embodiments 18 to 20, wherein reaction gas input mixture A comprises 40 to 60% by volume of $N_2$.

22. The process according to any of embodiments 4 to 21, wherein the methanol is oxidized to formaldehyde and water in reaction zone A at a reaction temperature in the range from 400 to 800° C.

23. The process according to any of embodiments 4 to 22, wherein the methanol is oxidized to formaldehyde and water in reaction zone A at a reaction temperature in the range from 500 to 800° C.

24. The process according to any of embodiments 4 to 22, wherein the methanol is oxidized to formaldehyde and water in reaction zone A at a reaction temperature in the range from 450 to 650° C., or from 500 to 600° C.

25. The process according to any of embodiments 4 to 22, wherein the methanol is oxidized to formaldehyde and water in reaction zone A at a reaction temperature in the range from 600 to 750° C.

26. The process according to any of embodiments 4 to 25, wherein the methanol is oxidized to formaldehyde and water in reaction zone A at a working pressure in the range from $10^3$ to $10^6$ Pa or from $10^4$ to $2·10^5$ Pa.

27. The process according to any of embodiments 1 to 3, wherein the at least one oxidation catalyst A has a catalytically active material which is a mixed oxide which has at least one transition metal in the oxidized state.

28. The process according to embodiment 27, wherein the at least one transition metal comprises Mo and/or V.

29. The process according to embodiment 27, wherein the at least one transition metal comprises Mo and Fe.

30. The process according to embodiment 27, wherein the catalytically active material is a mixed oxide of the general formula I $$[Fe_2(MoO_4)_3]_1[M^1{}_mO_n]_q \qquad (I)$$

in which the variables are each defined as follows:
$M^1$=Mo and/or Fe, or
  Mo and/or Fe and, based on the total molar amount of Mo and Fe, a total molar amount of up to 10 mol % (e.g. 0.01 to 10 mol %, or 0.1 to 10 mol %), preferably to an extent of not more than 5 mol %, of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B,
q=0 to 5,
m=1 to 3,
n=1 to 6.

31. The process according to embodiment 30, wherein q=0.5 to 3.

32. The process according to embodiment 30 or 31, wherein q=1 to 2.

33. The process according to any of embodiments 30 to 32, wherein $M^1$=Mo, m=1 and n=3.

34. The process according to any of embodiments 30 to 33, wherein $M^1$=Fe, m=2 and n=3.

35. The process according to any of embodiments 30 to 34, wherein less than 50 mol % of the Fe present in the mixed oxide I is present in the +2 oxidation state.

36. The process according to any of embodiments 30 to 34, wherein less than 20 mol % of the Fe present in the mixed oxide I is present in the +2 oxidation state.

37. The process according to any of embodiments 30 to 34, wherein less than 10 mol % of the Fe present in the mixed oxide I is present in the +2 oxidation state.

38. The process according to any of embodiments 30 to 34, wherein the entire amount of the Fe present in the mixed oxide I is present in the +3 oxidation state.

39. The process according to any of embodiments 30 to 38, wherein the ratio $n_{Mo}$:$n_{Fe}$, formed from the molar amount of Mo present in the mixed oxide I and the molar amount of Fe present in the same mixed oxide I, is 1:1 to 5:1.

40. The process according to any of embodiments 30 to 38, wherein the catalytically active material can be represented in a formal sense as a mixture of $MoO_3$ and $Fe_2O_3$, wherein the $MoO_3$ content of the mixture is 65 to 95% by weight and the $Fe_2O_3$ content of the mixture is 5 to 35% by weight.

41. The process according to any of embodiments 27 to 40, wherein the at least one oxidation catalyst A is an unsupported catalyst.

42. The process according to embodiment 41, wherein the geometry of the unsupported catalyst is selected from the group consisting of sphere, ring and solid cylinder.
43. The process according to embodiment 42, wherein the longest dimension of the unsupported catalyst is 1 to 10 mm.
44. The process according to embodiment 41, wherein the unsupported catalyst has the geometry of a ring with an external diameter of 3 to 10 mm, a height of 1 to 10 mm and an internal diameter of 1 to 8 mm.
45. The process according to embodiment 44, wherein the ring has a wall thickness of 1 to 3 mm.
46. The process according to any of embodiments 27 to 40, wherein the at least one oxidation catalyst A is an eggshell catalyst which has the catalytically active mixed oxide as an eggshell applied to the surface of an inert shaped support body.
47. The process according to embodiment 46, wherein the shaped support body is a sphere or a ring.
48. The process according to embodiment 47, wherein the longest dimension of the shaped support body is 1 to 10 mm.
49. The process according to embodiment 46, wherein the inert shaped support body is a ring with a length of 2 to 10 mm, an external diameter of 4 to 10 mm and a wall thickness of 1 to 4 mm.
50. The process according to any of embodiments 46 to 49, wherein the inert shaped support body is composed of steatite.
51. The process according to any of embodiments 46 to 50, wherein the eggshell of catalytically active mixed oxide has a thickness of 10 to 2000 µm, or 10 to 500 µm, or 100 to 500 µm, or 200 to 300 µm.
52. The process according to any of embodiments 27 to 51, wherein reaction gas input mixture A comprises not more than 15% by volume of methanol.
53. The process according to any of embodiments 27 to 51, wherein reaction gas input mixture A comprises not more than 11% by volume of methanol.
54. The process according to any of embodiments 27 to 53, wherein reaction gas input mixture A comprises 2 to 10% by volume of methanol.
55. The process according to any of embodiments 27 to 54, wherein reaction gas input mixture A comprises 6 to 9% by volume of methanol.
56. The process according to any of embodiments 27 to 55, wherein reaction gas input mixture A comprises the molecular oxygen in a molar amount $n_o$ and the methanol in a molar amount $n_{Me}$, and the $n_o:n_{Me}$ ratio is at least 1 or greater than 1.
57. The process according to embodiment 56, wherein the $n_o:n_{Me}$ ratio is 1.1 to 5.
58. The process according to embodiment 56 or 57, wherein the $n_o:n_{Me}$ ratio is 1.5 to 3.5.
59. The process according to any of embodiments 27 to 58, wherein reaction gas input mixture A comprises $N_2$ as at least one inert diluent gas other than steam.
60. The process according to embodiment 59, wherein reaction gas input mixture A comprises 70 to 95% by volume of $N_2$.
61. The process according to any of embodiments 27 to 60, wherein reaction gas input mixture A comprises 0 to 20% by volume of $H_2O$.
62. The process according to embodiment 61, wherein reaction gas input mixture A comprises 0.1 to 10% by volume of $H_2O$.
63. The process according to embodiment 61 or 62, wherein reaction gas input mixture A comprises 0.2 to 7% by volume of $H_2O$.
64. The process according to any of embodiments 60 to 62, wherein reaction gas input mixture A comprises 0.5 to 5% by volume of $H_2O$.
65. The process according to any of embodiments 27 to 64, wherein the methanol is oxidized to formaldehyde and water in reaction zone A at a reaction temperature in the range from 250 to 500° C.
66. The process according to embodiment 65, wherein the methanol is oxidized to formaldehyde and water in reaction zone A at a reaction temperature in the range from 250 to 400° C.
67. The process according to any of embodiments 27 to 66, wherein the methanol is oxidized to formaldehyde and water in reaction zone A at a working pressure in the range from $10^3$ to $10^6$ Pa or from $10^4$ to $2 \cdot 10^5$ Pa.
68. The process according to embodiment 67, wherein a portion of the stream Y is recycled into reaction zone A to obtain reaction gas input mixture A.
69. The process according to any of embodiments 1 to 68, wherein the acetic acid present in the at least one further stream is acetic acid obtained by homogeneous catalysis catalyzed carbonylation of methanol in the liquid phase.
70. The process according to embodiment 69, wherein the catalyst comprises Rh in combination with HI and $CH_3I$.
71. The process according to embodiment 69 or 70, wherein the acetic acid present in the at least one further stream is acetic acid removed by rectification from the product mixture of the homogeneously catalyzed carbonylation of methanol to acetic acid in the liquid phase.
72. The process according to any of embodiments 1 to 68, wherein the at least one further stream comprising acetic acid is the product gas mixture of a heterogeneously catalyzed gas phase carbonylation of methanol to acetic acid in the absence of halogenated compounds.
73. The process according to any of embodiments 1 to 72, wherein the reaction temperature in reaction zone B is 200 to 400° C.
74. The process according to any of embodiments 1 to 72, wherein the reaction temperature in reaction zone B is 280 to 380° C.
75. The process according to any of embodiments 1 to 72, wherein the reaction temperature in reaction zone B is 300 to 370° C.
76. The process according to any of embodiments 1 to 75, wherein the working pressure in reaction zone B is $1.2 \cdot 10^5$ Pa to $50 \cdot 10^5$ Pa.
77. The process according to any of embodiments 1 to 76, wherein the formaldehyde content of reaction gas input mixture B is 0.5 to 10% by volume.
78. The process according to any of embodiments 1 to 76, wherein the formaldehyde content of reaction gas input mixture B is 0.5 to 7% by volume.
79. The process according to any of embodiments 1 to 76, wherein the formaldehyde content of reaction gas input mixture B is 1 to 5% by volume.
80. The process according to any of embodiments 1 to 79, wherein reaction gas input mixture B comprises acetic acid in a molar amount $n_{HAc}$ and formaldehyde in a molar amount $n_{Fd}$, and the $n_{HAc}:n_{Fd}$ ratio is greater than 1 and ≤10.
81. The process according to embodiment 80, wherein the $n_{HAc}:n_{Fd}$ ratio is 1.1 to 5.
82. The process according to embodiment 80, wherein the $n_{HAc}:n_{Fd}$ ratio is 1.5 to 3.5.

83. The process according to any of embodiments 1 to 82, wherein the acetic acid content of reaction gas input mixture B is 1.5 to 20% by volume.
84. The process according to any of embodiments 1 to 82, wherein the acetic acid content of reaction gas input mixture B is 2 to 15% by volume.
85. The process according to any of embodiments 1 to 82, wherein the acetic acid content of reaction gas input mixture B is 3 to 10% by volume.
86. The process according to any of embodiments 1 to 85, wherein the molecular oxygen content of reaction gas input mixture B is 0.5 to 5% by volume.
87. The process according to any of embodiments 1 to 85, wherein the molecular oxygen content of reaction gas input mixture B is 2 to 5% by volume.
88. The process according to any of embodiments 1 to 87, wherein the steam content of reaction gas input mixture B does not exceed 30% by volume and is not less than 0.5% by volume.
89. The process according to any of embodiments 1 to 87, wherein the steam content of reaction gas input mixture B does not exceed 20% by volume and is not less than 1% by volume.
90. The process according to any of embodiments 1 to 87, wherein the steam content of reaction gas input mixture B is 0.5 to 15% by volume or 1 to 10% by volume.
91. The process according to any of embodiments 1 to 90, wherein the content of inert diluent gas other than steam in reaction gas input mixture B is at least 30% by volume or at least 40% by volume.
92. The process according to any of embodiments 1 to 90, wherein the content of inert diluent gas other than steam in reaction gas input mixture B is at least 50% by volume.
93. The process according to any of embodiments 1 to 92, wherein reaction gas input mixture B comprises, as at least one inert diluent gas other than steam, at least 30% by volume or at least 40% by volume of $N_2$.
94. The process according to any of embodiments 1 to 92, wherein reaction gas input mixture B comprises, as at least one inert diluent gas other than steam, at least 50% by volume of $N_2$.
95. The process according to any of embodiments 1 to 94, wherein the at least one aldol condensation catalyst B is a zeolite with anionic structural charge, on whose inner and outer surfaces at least one cation type from the group of the alkali metal ions and alkaline earth metal ions is present, in order to neutralize the negative structural charge.
96. The process according to any of embodiments 1 to 94, wherein the at least one aldol condensation catalyst B is hydroxide from the group consisting of alkali metal hydroxides, alkaline earth metal hydroxides and aluminum hydroxide applied to amorphous silicon dioxide.
97. The process according to embodiment 96, wherein the hydroxide applied to the amorphous silicon dioxide is KOH, NaOH, $Ca(OH)_2$ or $Mg(OH)_2$.
98. The process according to any of embodiments 1 to 94, wherein the at least one aldol condensation catalyst B is a catalyst which comprises
   as constituent a), at least one oxide of at least one of the elements Si, Al, Ti, Zr, Cd, Sn, Ga, Y and La and/or zeolite, and
   as constituent b), at least one oxide selected from boron oxide and phosphorus oxide, and optionally
   as constituent c), one or more than one oxide of at least one of the elements V, Cr, Co, Ni, Mo and Pb and/or more than one heteropolyacid with at least one poly atom selected from V, Mo and W.
99. The process according to embodiment 98, wherein the at least one aldol condensation catalyst B comprises 1 to 50% by weight of boron oxide, or 1 to 50% by weight of phosphorus oxide, or 1 to 50% by weight of boron oxide and phosphorus oxide, where the boron oxide, based on the amount of B present, is always calculated as $B_2O_3$ and the phosphorus oxide, based on the amount of P present, is always calculated as $P_2O_5$.
100. The process according to any of embodiments 1 to 94, wherein the at least one aldol condensation catalyst B has a catalytically active material which is a vanadium-phosphorus oxide or a vanadium-phosphorus oxide doped with elements other than vanadium and phosphorus.
101. The process according to embodiment 100, wherein the catalytically active material is a multielement oxide active material of the general formula II $$V_1P_bFe_cX^1_dX^2_eO_n \qquad (II)$$

in which the variables are each defined as follows:
$X^1$=Mo, Bi, Co, Ni, Si, Zn, Hf, Zr, Ti, Cr, Mn, Cu, B, Sn and/or Nb,
$X^2$=Li, K, Na, Rb, Cs and/or Tl,
b=0.9 to 2.0
c=≥0 to 0.1,
d=≥0 to 0.1,
e=≥0 to 0.1, and
n=the stoichiometric coefficient of the element oxygen, which is determined by the stoichiometric coefficients of the non-oxygen elements and the charge numbers thereof in II.
102. The process according to embodiment 101, wherein $X^1$=Nb, Mo, Zn and/or Hf.
103. The process according to embodiment 101 or 102, wherein b is 0.9 to 1.5.
104. The process according to embodiment 101 or 102, wherein b is 0.9 to 1.2.
105. The process according to any of embodiments 101 to 104, wherein $X^1$=Mo.
106. The process according to any of embodiments 101 to 105, wherein c is 0.005 to 0.1.
107. The process according to any of embodiments 101 to 105, wherein c is 0.005 to 0.05 or 0.005 to 0.02.
108. The process according to embodiment 100, wherein the ratio $n_p:n_v$ of the molar amount $n_p$ of phosphorus present in the catalytically active material to the molar amount $n_v$ of V present in the catalytically active material is 0.09 to 2.0, preferably 0.9 to 1.5 and more preferably 0.9 to 1.2.
109. The process according to either of embodiments 100 or 108, wherein the elements other than vanadium and phosphorus present in the catalytically active material are one or more than one element from the group consisting of lithium, potassium, sodium, rubidium, cesium, thallium, molybdenum, zinc, hafnium, zirconium, titanium, chromium, manganese, nickel, copper, iron, boron, silicon, tin, niobium, cobalt and bismuth.
110. The process according to embodiment 109, wherein the total content of elements other than vanadium and phosphorus in the catalytically active material, based on the weight thereof, is not more than 5% by weight, calculating the particular element other than vanadium and phosphorus as the electrically neutral oxide in which the element has the same charge number as in the active material.
111. The process according to any of embodiments 100 to 110, wherein the arithmetic mean oxidation state of vanadium in the catalytically active material is +3.9 to +4.4 or +4.0 to +4.3.

112. The process according to any of embodiments 100 to 111, wherein the specific BET surface area of the catalytically active material is ≥15 to 50 m²/g.
113. The process according to any of embodiments 100 to 112, wherein the total pore volume of the catalytically active material is 0.1 to 0.5 ml/g.
114. The process according to any of embodiments 100 to 113, wherein the total pore volume of the catalytically active material is 0.15 to 0.4 ml/g.
115. The process according to any of embodiments 100 to 114, wherein the at least one oxidation catalyst B is an unsupported catalyst or a supported catalyst.
116. The process according to embodiment 115, wherein the geometry of the unsupported catalyst is selected from the group consisting of sphere, ring and solid cylinder, and has a longest dimension in the range from 1 to 10 mm.
117. The process according to embodiment 115, wherein the geometry of the unsupported catalyst is a ring (a hollow cylinder) with an external diameter in the range from 3 to 10 mm, a height of 1 to 10 mm, an internal diameter of 1 to 8 mm and a wall thickness of 1 to 3 mm.
118. The process according to any of embodiments 100 to 114, wherein the at least one aldol condensation catalyst B is an eggshell catalyst which has the catalytically active material as an eggshell applied to the surface of an inert shaped support body.
119. The process according to embodiment 118, wherein the shaped support body is a sphere or a ring.
120. The process according to embodiment 118 or 119, wherein the longest dimension of the shaped support body is 1 to 10 mm.
121. The process according to any of embodiments 118 to 120, wherein the inert shaped support body is composed of steatite.
122. The process according to any of embodiments 118 to 121, wherein the thickness of the eggshell of active material is 10 to 2000 μm, or 10 to 500 μm, or 100 to 500 μm, or 200 to 300 μm.
123. The process according to any of embodiments 1 to 122, wherein product gas mixture B is separated in separation zone T by passing product gas mixture B, optionally after direct and/or indirect cooling thereof, into a condensation column equipped with separating internals and fractionally condensing it within the condensation column and conducting streams X, Y and Z out of the condensation column as separate fractions.
124. The process according to any of embodiments 1 to 123, wherein product gas mixture B is separated in separation zone T by passing product gas mixture B, optionally after direct and/or indirect cooling thereof, into an absorption column equipped with separating internals in countercurrent to an organic solvent with a higher boiling point than acrylic acid at standard pressure, and absorbing the acetic acid and acrylic acid present in product gas mixture B into the solvent to obtain an absorbate, while a stream Z leaves the absorption column at the top thereof, and then removing streams X and Y from the absorbate as separate fractions by fractional distillation thereof in a rectification column.
125. The process according to any of embodiments 1 to 123, wherein product gas mixture B is separated in separation zone T by passing product gas mixture B, optionally after direct and/or indirect cooling thereof, into an absorption column equipped with separating internals in countercurrent to an aqueous solution as an absorbent, and absorbing the acetic acid and acrylic acid present in product gas mixture B into the solvent to obtain an absorbate, while a stream Z leaves the absorption column at the top thereof, and then removing streams X and Y as separate fractions from the absorbate by fractional distillation thereof in a rectification column.
126. Acrylic acid for which the ratio V of the molar amount $n^{14}C$ of $^{14}C$ atomic nuclei present in this acrylic acid to the molar amount $n^{12}C$ of $^{12}C$ atomic nuclei present in the same acrylic acid, $V=n^{14}C:n^{12}C$, is greater than 0 and less than the corresponding molar ratio $V^*$ of $^{14}C$ atomic nuclei to $^{12}C$ atomic nuclei present in the carbon dioxide in the earth's atmosphere.
127. Acrylic acid according to embodiment 126, wherein $V=(1/3) \cdot V^*$.
128. Acrylic acid according to embodiment 126, wherein $V=(2/3) \cdot V^*$.
129. A liquid phase P comprising at least 1 kg of acrylic acid, wherein the acrylic acid present is an acrylic acid according to any of embodiments 126 to 128.

EXAMPLES

I) Preparation of Different Catalysts

A) Preparation of a mixed oxide catalyst for the heterogeneously catalyzed partial gas phase oxidation of methanol to formaldehyde by the FORMOX process.

530 g of ammonium heptamolybdate tetrahydrate $((NH_4)_6Mo_7O_{24} \cdot 4H_2O)$ were dissolved in a mixture, at a temperature of 60° C., of 800 ml of water and 250 g of a 25% by weight aqueous ammonia solution while maintaining the 60° C. This gave a solution 1 at 60° C.

808 g of iron(III) nitrate nonahydrate $(Fe(NO_3)_3 \cdot 9H_2O)$ were dissolved in 1000 ml of water at 60° C. while maintaining the 60° C. This gave a solution 2 at 60° C.

Within 20 min, solution 2 was stirred continuously into solution 1 while maintaining the 60° C. Subsequently, the mixture was stirred at 60° C. for another 5 min. The aqueous suspension obtained was subsequently spray-dried at an inlet temperature of 340° C. and an outlet temperature of 110° C. in an air stream within 1.5 h (spray tower of the Mobile Minor 2000 (MM-I) type from Niro A/S, Gladsaxevej 305, 2860 Soborg, Denmark, with a centrifugal atomizer of the F01A type and an atomizer wheel of the SL24-50 type). During the spray drying, stirring of the proportion of the suspension which was yet to be sprayed in each case was continued while maintaining the 60° C.

The spray powder thus obtained was, based on its weight, mixed homogeneously with 1% by weight of TIMREX® T44 graphite from Timcal AG (cf. WO 2008/087116) (in a drum hoop mixer; wheel diameter: 650 mm, drum volume: 5 l, speed: approx. 30 rpm, mixing time: 30 min). The resulting mixture was then compacted in a roll compactor of the RCC 100×20 type from Powtec with 2 contrarotary steel rollers with a pressure of 12 bar, and then forced through a screen with square meshes of mesh size 0.8 mm. The resulting compactate (which had a bulk density of 1050 g/l and an approximately homogeneous particle size of ≥0.4 mm and ≥0.8 mm) was subsequently mixed in the aforementioned drum hoop mixer at speed of approx. 30 rpm within 30 min with, based on its weight, 3% by weight of the same graphite, and then compacted as described in DE-A 10 2008040093 to annular shaped unsupported catalyst precursor bodies of geometry 5 mm×3 mm×3 mm (external diameter×height×internal diameter) with a side crushing strength of 22±5 N and a mass of 130 mg (fill height: 7.5-9 mm; pressing force: 3.0-3.5 kN; Kilian rotary tableting press (9-die tableting machine) of the S100 type (from Kilian, D-50735 Cologne). The tableting was effected under a nitrogen atmosphere.

For the final thermal treatment, the shaped catalyst precursor bodies were divided homogeneously between 4 grids arranged alongside one another with a square base area of in each case 150 mm×150 mm (bed height: approx. 40 mm) and treated in a forced-air oven with air flow (from Heraeus Instruments GmbH, D-63450 Hanau, model: K 750/2) as follows: the air flow was 100 l (STP)/h and initially had a temperature of 120° C. The 120° C. was first maintained for 10 h. Then the temperature was increased to 460° C. in an essentially linear manner within 10 h, and the 460° C. was then maintained for a further 4 h. This was followed by cooling to 25° C. within 5 h.

An annular unsupported oxidation catalyst A was thus obtained, the mixed oxide active material of which had the stoichiometry $Fe_2(MoO_4)_3$. Subsequently, the unsupported catalyst rings were forced through a screen with square meshes of mesh size 0.8 mm. The material passing through the screen (spall of oxidation catalyst A) had an essentially homogeneous particle size (longest dimension) of ≥0.4 mm and ≤0.8 mm.

B) Production of an aldol condensation catalyst B whose active material is a vanadium-phosphorus oxide doped with Fe(III)

A stirred tank which was heatable externally with molecular nitrogen ($N_2$ content ≥99.99% by volume) and by means of pressurized water, had an internal volume of 8 m³, was enameled on the inner surface thereof and was equipped with baffles and an impeller stirrer was initially charged with 4602 kg of isobutanol. After the three-level impeller stirrer had been started, the isobutanol was heated to 90° C. under reflux. While maintaining this temperature, continuous supply of 690 kg of finely divided vanadium pentoxide via a conveying screw was then commenced. Once 460 kg of vanadium pentoxide ($V_2O_5$) had been added within 20 min, while continuing the supply of vanadium pentoxide, the continuous pumped addition of 805 kg of 105% by weight phosphoric acid (cf. DE-A 3520053) was commenced, in the course of which the temperature of 90° C. was maintained (pumping rate=160 kg/h).

After the addition of the phosphoric acid had ended, the mixture was heated while stirring and under reflux to temperatures in the range from 100 to 108° C. and kept within this temperature range for 14 hours. Subsequently, the hot suspension obtained was cooled to 60° C. in an essentially linear manner within 75 minutes, and 22.7 kg of iron(III) phosphate hydrate were added (Fe content: 29.9% by weight; supplier: Dr. Paul Lohmann; free of Fe(II) impurities). Then the mixture was heated, again under reflux, to temperatures of 100 to 108° C., and the suspension was kept at this temperature while continuing to stir for 1 hour. Subsequently, the suspension at approx. 105° C. was discharged into a pressure suction filter which had been inertized beforehand with nitrogen and heated to 100° C., and filtered at a pressure above the suction filter of approx. 0.35 MPa abs. The filtercake obtained was blown dry by constantly introducing nitrogen while stirring and at 100° C. within one hour. After blowing dry, the filtercake was heated to 155° C. and evacuated to a pressure of 15 kPa abs. (150 mbar abs.).

Under these conditions, the drying was performed down to a residual isobutanol content of 2% by weight in the dried precursor material. This comprised Fe and V in a molar Fe/V ratio of 0.016.

Subsequently, the dry powder was treated further in an inclined stainless steel rotating tube through which 100 m³/h of air (the entrance temperature of which was 150° C.) flowed and which had internal spiral winding. The tube length was 6.5 m, the internal diameter 0.9 m and the rotary tube wall thickness 2.5 cm. The speed of rotation of the tube was 0.4 rpm. The dry powder was supplied to the tube interior in an amount of 60 kg/h at the upper end thereof. The spiral winding ensured homogeneous flowing motion (downward) of the dry powder within the rotating tube. The rotating tube length was divided into five heating zones of the same length, the temperature of which was controlled from the outside. The temperatures of the five heating zones measured on the outer wall of the rotating tube were, from the top downward, 250° C., 300° C., 345° C., 345° C. and 345° C.

400 g of the powder leaving the rotating tube were, based on the weight thereof, mixed homogeneously with 1% by weight of graphite (Asbury 3160, from Timcal Ltd., cf. WO 2008/087116) (in a drum hoop mixer of wheel diameter 650 mm, drum volume 5 l, speed: 30 rpm, mixing time: 30 min). The resulting mixture was then compacted with the aid of a Powtec roll compactor with 2 contrarotary steel rolls at an applied pressure of 9 bar, and then forced through a screen with square screen meshes of size 1 mm. The resulting compactate had a bulk density of 1100 g/l and an essentially homogeneous particle size of ≥0.7 mm and ≤0.8 mm. 30 ml of bed volume of the granules were charged into a vertical tube furnace (tube diameter: 26 mm; in the center of the tube, thermowell running from the top downward with an external diameter of 4 mm to accommodate a thermocouple). 25 l (STP)/h of air with an inlet temperature of 160° C. were conducted through the tube furnace. At a heating rate of 5° C./min, the temperature of the calcination material present in the tube furnace was increased from 25° C. to 250° C. On attainment of the temperature of 250° C., the temperature of the calcination material was raised at a heating rate of 2° C./min to 330° C. This temperature was maintained over a period of 40 min.

Then, while maintaining a volume flow of 25 l (STP)/h, air flow was switched to a flow of a mixture of 50% by volume of $N_2$ and 50% by volume of steam (the inlet temperature of which was 160° C.) through the tube furnace, and the temperature of the calcination material was raised at a heating rate of 3° C./min to 425° C. This temperature was maintained over a period of 180° C. Then, while maintaining the volume flow rate of 25 l (STP)/h, the flow was switched again to an air flow (the inlet temperature of the air stream was 25° C.). Then the temperature of the calcination material was cooled to 25° C. within 120 min.

The stoichiometry of the Fe(III)-doped vanadium-phosphorus oxide unsupported aldol condensation catalyst B prepared as described was $V_1P_{1.05}Fe_{0.016}O_n$.

II) Performance of a process according to the invention for preparing acrylic acid from acetic acid and methanol using the catalysts prepared in I) (the contents of all reaction gas input mixtures and reactants were determined by gas chromatography)

1. Configuration of Reaction Zone A

Reaction zone A was implemented in a tubular reactor A (internal diameter: 8 mm; wall thickness: 1 mm; length: 100 mm; material: stainless steel, DIN material 1.4541), which was electrically heatable externally. The catalyst charge in tubular reactor A was configured as follows:

30 mm of a preliminary bed of steatite spall (longest dimension 1 to 1.5 mm; C220 steatite from CeramTec) at the reactor inlet; and 64 mm with 3.24 ml of the spall of oxidation catalyst A.

The contents of reaction gas input mixture A were:

9.15% by vol. of methanol, 3.04% by vol. of water, 77.76% by vol. of $N_2$, and 10.05% by vol. of $O_2$.

Reaction gas input mixture A (21.0 l (STP)/h) was supplied to the preliminary bed of steatite spall with an inlet temperature of 265° C. The pressure at the inlet into the tubular reactor A was 2 bar abs. The temperature of the tubular reactor A was set to 265° C. over the length of the fixed bed charge thereof (outer wall temperature of tubular reactor A). The remaining length of tubular reactor A was unheated. The space velocity on the catalyst charge of reaction gas input mixture C was 6500 h$^{-1}$.

The product gas mixture A leaving the tubular reactor A (22.0 l (STP)/h) had the following contents (online GC analysis):

0.07% by vol. of methanol,
8.03% by vol. of formaldehyde,
11.84% by vol. of water,
73.71% by vol. of $N_2$,
4.83% by vol. of $O_2$,
0.40% by vol. of $CO_2$,
0.09% by vol. formic acid, and
0.04% by vol. of dimethyl ether.

2. Configuration of Reaction Zone B

Reaction zone B was implemented in a tubular reactor B (internal diameter: 15 mm; wall thickness: 1.2 mm; length: 2000 mm; material: stainless steel, DIN material 1.4541), which was electrically heatable externally. The catalyst charge in tubular reactor B was configured as follows:

1000 mm of a preliminary bed of steatite spall (as in reaction zone A) at the reactor inlet; and
753 mm with 133 ml of the unsupported aldol condensation catalyst B.

The 22.0 l (STP)/h of the formaldehyde-comprising product gas mixture A, 20.5 l (STP)/h of a gaseous mixture of molecular nitrogen and acetic acid converted to the vapor phase (99% by volume of acetic acid), which had the following contents:

90.49% by vol. of $N_2$, and
8.49% by vol. of acetic acid, and 2.6 l (STP)/h of acetic acid converted to the vapor phase (which formed stream Y) were used to obtain 45.1 l (STP)/h of reaction gas input mixture B.

The contents of the vaporized acetic acid were:
99% by vol. of acetic acid.
The contents of reaction gas input mixture B were:
0.03% by vol. of methanol,
3.91% by vol. of formaldehyde,
5.76% by vol. of water,
76.83% by vol. of $N_2$,
2.35% by vol. of $O_2$,
9.86% by vol. of acetic acid,
0.19% by vol. of $CO_2$,
0.04% by vol. of formic acid, and
0.02% by vol. of dimethyl ether.

Reaction gas input mixture B was supplied to the preliminary bed of steatite spall with an inlet temperature of 320° C. The pressure at the inlet into tubular reactor B was 1.5 bar abs. The temperature of tubular reactor B was set to 340° C. over the length of the fixed bed thereof (outer wall temperature of tubular reactor B). The remaining length of tubular reactor B was unheated. The space velocity on the catalyst charge of reaction gas input mixture B was 340 h$^{-1}$ (l (STP)/l·h).

The product gas mixture B leaving the tubular reactor B (45.1 l (STP)/h) had the following contents (online GC analysis):

0.03% by vol. of methanol,
0.04% by vol. of formaldehyde,
9.63% by vol. of water,
76.83% by vol. of $N_2$,
2.27% by vol. of $O_2$,
3.76% by vol. of acrylic acid,
6.04% by vol. of acetic acid,
0.28% by vol. of $CO_2$,
0.04% by vol. of formic acid, and
0.02% by vol. of dimethyl ether.

Based on the amount of methanol supplied to reaction zone A, the yield of acrylic acid achieved was 88 mol %.

Including acetic acid preparation by homogeneously catalyzed carbonylation of methanol in the liquid phase with a selectivity of acetic acid formation of ≥99 mol %, the yield of acrylic acid, based on the total amount of methanol used for preparation thereof, is approx. 95.3 mol %.

US Provisional Patent Application No. 61/383363, filed Sep. 16, 2010, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

The invention claimed is:

1. A process for preparing acrylic acid from methanol and acetic acid, which comprises the following measures:

a stream of a reaction gas input mixture A comprising the methanol and molecular oxygen reactants and at least one inert diluent gas other than steam is conducted through a first reaction zone A charged with at least one oxidation catalyst A and, in the course of passage through reaction zone A, methanol present in the reaction gas input mixture A is oxidized under heterogeneous catalysis to formaldehyde and steam so as to form a product gas mixture A comprising formaldehyde, steam and at least one inert diluent gas other than steam, with or without excess molecular oxygen, and a stream of product gas mixture A leaves reaction zone A, producing a stream of a reaction gas input mixture B by mixing the stream of product gas mixture A and at least one further stream comprising acetic acid such that reaction gas input mixture B comprises acetic acid, steam, at least one inert diluent gas other than steam and formaldehyde, with or without molecular oxygen, and in which the molar amount $n_{HAc}$ of acetic acid present is greater than the molar amount $n_{Fd}$ of formaldehyde present therein, the stream of reaction gas input mixture B is passed through a second reaction zone B charged with at least one aldol condensation catalyst B and formaldehyde present in reaction gas input mixture B, as it flows through reaction zone B, is condensed with acetic acid present in reaction gas input mixture B under heterogeneous catalysis to give acrylic acid and $H_2O$, so as to form a product gas mixture B comprising acrylic acid, acetic acid, steam and at least one inert diluent gas other than steam, with or without molecular oxygen, and a stream of product gas mixture B leaves reaction zone B, the stream of product gas mixture B leaving reaction zone B is fed to a separation zone T and separated in separation zone T into at least three streams X, Y and Z, the acrylic acid content in percent by weight present in stream X being greater than the acrylic acid content in percent by weight present in streams Y and Z together, the acetic acid content in percent by weight present in stream Y being greater than the acetic acid content in percent by weight present in streams X and Z together, the content in percent by volume of inert diluent gas other than steam present in stream Z being greater than the content in percent by volume of inert diluent gas other than steam present in streams X and Y together, and stream Y is recycled into reaction zone B and used to obtain reaction gas input mixture B wherein product gas mixture B is separated in separation zone T by a method selected from the group consisting of:

product gas mixture B is separated in separation zone T by passing product gas mixture B into a condensation column equipped with separating internals and fractionally condensing it within the condensation column and conducting streams X, Y and Z out of the condensation column as separate fractions, product gas mixture B is separated in separation zone T by passing product gas mixture B into an absorption column equipped with separating internals in countercurrent to an organic solvent with a higher boiling point than acrylic acid at standard pressure, and absorbing the acetic acid and acrylic acid present in product gas mixture B into the solvent to obtain an absorbate, while a stream Z leaves the absorption column at the top thereof, and then removing streams X and Y from the absorbate as separate fractions by fractional distillation thereof in a rectification column, and product gas mixture B is separated in separation zone T by passing product gas mixture B into an absorption column equipped with separating internals in countercurrent to an aqueous solution as an absorbent, and absorbing the acetic acid and acrylic acid present in product gas mixture B into the solvent to obtain an absorbate, while a stream Z leaves the absorption column at the top thereof, and then removing streams X and Y as separate fractions from the absorbate by fractional distillation thereof in a rectification column.

2. The process according to claim 1, wherein the at least one oxidation catalyst A comprises a catalytically active material which is a mixed oxide of the general formula I $$[Fe_2(MoO_4)_3]_1 [M^1_m O_n]_q \qquad (I)$$

in which the variables are each defined as follows:

$M^1$=Mo and/or Fe, or

Mo and/or Fe and, based on the total molar amount of Mo and Fe, a total molar amount of up to 10 mol % of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B, q=0 to 5, m=1 to 3, n=1 to 6.

3. The process according to claim 1, wherein reaction gas input mixture A comprises 2 to 15% by volume of methanol.

4. The process according to claim 1, wherein reaction gas input mixture A comprises 0 to 20% by volume of $H_2O$.

5. The process according to claim 1, wherein reaction gas input mixture A comprises the molecular oxygen in a molar amount $n_o$ and the methanol in a molar amount $n_{Me}$, and the $n_O$: $n_{Me}$ ratio is at least 1 or greater than 1.

6. The process according to claim 1, wherein a portion of the stream Y is recycled into reaction zone A to obtain reaction gas input mixture A.

7. The process according to claim 1, wherein reaction gas input mixture A comprises $N_2$ as the at least one inert diluent gas other than steam.

8. The process according to claim 1, wherein the methanol is oxidized to formaldehyde and water in reaction zone A at a reaction temperature in the range from 250 to 400° C.

9. The process according to claim 1, wherein the acetic acid present in the at least one further stream is acetic acid obtained by homogeneous catalysis catalyzed carbonylation of methanol in the liquid phase.

10. The process according to claim 9, wherein the catalyst comprises Rh in combination with HI and $CH_3I$.

11. The process according to claim 9, wherein the acetic acid present in the at least one further stream is acetic acid removed by rectification from the product mixture of the homogeneously catalyzed carbonylation of methanol to acetic acid in the liquid phase.

12. The process according to claim 1, wherein the at least one further stream comprising acetic acid is the product gas mixture of a heterogeneously catalyzed gas phase carbonylation of methanol to acetic acid in the absence of halogenated compounds.

13. The process according to claim 1, wherein the reaction temperature in reaction zone B is 200 to 400° C.

14. The process according to claim 1, wherein the formaldehyde content in reaction gas input mixture B is 0.5 to 10% by volume.

15. The process according to claim 1, wherein reaction gas input mixture B comprises acetic acid in a molar amount $n_{HAc}$ and formaldehyde in a molar amount $n_{Fd}$, and the $n_{HAc}$:$n_{Fd}$ ratio is greater than 1 and ≤10.

16. The process according to claim 1, wherein the acetic acid content of reaction gas input mixture B is 1.5 to 20% by volume.

17. The process according to claim 1, wherein the steam content of reaction gas input mixture B does not exceed 30% by volume and is not less than 0.5% by volume.

18. The process according to claim 1, wherein the at least one aldol condensation catalyst B has a catalytically active material which is a multielement oxide active material of the general formula II $$V_i P_b Fe_c X^1_d X^2_e O_n \qquad (II)$$

in which the variables are each defined as follows:

$X^1$=Mo, Bi, Co, Ni, Si, Zn, Hf, Zr, Ti, Cr, Mn, Cu, B, Sn and/or Nb, $X^2$=Li, K, Na, Rb, Cs and/or Tl, b=0.9 to 2.0 c=≥0 to 0.1, d=≥0 to 0.1, e=≥0 to 0.1, and n=the stoichiometric coefficient of the element oxygen, which is determined by the stoichiometric coefficients of the non-oxygen elements and the charge numbers thereof in II.

19. The process according to claim 1, wherein product gas mixture B is separated in separation zone T by passing product gas mixture B into a condensation column equipped with separating internals and fractionally condensing it within the condensation column and conducting streams X, Y and Z out of the condensation column as separate fractions.

20. The process according to claim 1, wherein product gas mixture B is separated in separation zone T by passing product gas mixture B into an absorption column equipped with separating internals in countercurrent to an organic solvent with a higher boiling point than acrylic acid at standard pressure, and absorbing the acetic acid and acrylic acid present in product gas mixture B into the solvent to obtain an absorbate, while a stream Z leaves the absorption column at the top thereof, and then removing streams X and Y from the absorbate as separate fractions by fractional distillation thereof in a rectification column.

21. The process according to claim 1, wherein product gas mixture B is separated in separation zone T by passing product gas mixture B into an absorption column equipped with separating internals in countercurrent to an aqueous solution as an absorbent, and absorbing the acetic acid and acrylic acid present in product gas mixture B into the solvent to obtain an absorbate, while a stream Z leaves the absorption column at the top thereof, and then removing streams X and Y as separate fractions from the absorbate by fractional distillation thereof in a rectification column.

22. The process according to claim 1, wherein the stream of product gas mixture A leaving reaction zone A is fed to a separation zone T* and any unconverted methanol still present in product gas mixture A in separation zone T* is removed from product gas mixture A to leave a formaldehyde-comprising product gas mixture A*, and a stream of product gas mixture A* is obtained which is used as product gas mixture A for subsequent steps in said process.

23. The process according to claim 1, wherein further molecular oxygen and/or further inert diluent gas is supplied to the reaction gas mixture A flowing through reaction zone A on its way through reaction zone A.

24. The process according to claim 1, wherein further molecular oxygen and/or further inert diluent gas is supplied to the reaction gas mixture B flowing through reaction zone B on its way through reaction zone B.

25. The process according to claim 19, wherein product gas mixture B is separated in separation zone T by passing product gas mixture B after direct cooling thereof into said condensation column equipped with separating internals.

26. The process according to claim 19, wherein product gas mixture B is separated in separation zone T by passing product gas mixture B after indirect cooling thereof into said condensation column equipped with separating internals.

27. The process according to claim 20, wherein product gas mixture B is separated in separation zone T by passing product gas mixture B after direct cooling thereof into said absorption column equipped with separating internals.

28. The process according to claim 20, wherein product gas mixture B is separated in separation zone T by passing product gas mixture B after indirect cooling thereof into said absorption column equipped with separating internals.

29. The process according to claim 21, wherein product gas mixture B is separated in separation zone T by passing product gas mixture B after direct cooling thereof into said absorption column equipped with separating internals.

30. The process according to claim 21, wherein product gas mixture B is separated in separation zone T by passing product gas mixture B after indirect cooling thereof into said absorption column equipped with separating internals.

* * * * *